(12) United States Patent
Franke et al.

(10) Patent No.: US 7,491,196 B2
(45) Date of Patent: Feb. 17, 2009

(54) ABSORBENT GARMENT

(75) Inventors: Mark S. Franke, Neenah, WI (US);
Kristi J. Bryant, Appleton, WI (US);
Cynthia H. Hendren, Oshkosh, WI
(US); Richard J. Kamps, Wrightstown,
WI (US); David A. Kuen, Neenah, WI
(US); Lisa Nickel, Menasha, WI (US);
Katherine C. Wheeler, Menasha, WI
(US); Yee Yang, Appleton, WI (US)

(73) Assignee: Kimberly-Clark Worldwide, Inc.,
Neenah, WI (US)

( * ) Notice: Subject to any disclaimer, the term of this patent is extended or adjusted under 35 U.S.C. 154(b) by 904 days.

(21) Appl. No.: 10/735,978

(22) Filed: Dec. 15, 2003

(65) Prior Publication Data

US 2005/0131377 A1 Jun. 16, 2005

(51) Int. Cl.
*A61F 13/15* (2006.01)
*A61F 13/20* (2006.01)
(52) U.S. Cl. .................. 604/396; 604/397
(58) Field of Classification Search ............ 604/385.14, 604/393–396
See application file for complete search history.

(56) References Cited

U.S. PATENT DOCUMENTS

| | | |
|---|---|---|
| 1,664,298 A | 3/1928 | Katz |
| 1,971,558 A | 8/1934 | Goodman |
| 2,030,306 A | 2/1936 | Lain |
| 2,088,302 A | 7/1937 | McKeever |
| 2,252,019 A | 8/1941 | Meinecke et al. |
| 2,450,789 A | 10/1948 | Frieman |
| 2,566,325 A | 9/1951 | Ganz |
| 2,675,806 A | 4/1954 | Bram |
| 2,711,735 A | 6/1955 | Sabo |
| 2,838,047 A | 6/1958 | Sidnell |

(Continued)

FOREIGN PATENT DOCUMENTS

AT 168 478 6/1951

(Continued)

OTHER PUBLICATIONS

International Search Report for PCT/US2004/021614 dated Nov. 25, 2004, 5 pages.

(Continued)

*Primary Examiner*—Tatyana Zalukaeva
*Assistant Examiner*—Melanie J Hand
(74) *Attorney, Agent, or Firm*—Armstrong Teasdale, LLP

(57) ABSTRACT

An absorbent garment has an absorbent assembly disposed within a garment shell configured for encircling a wearer's waist. The absorbent assembly has an inner surface adapted for contiguous relationship with the wearer's body, a front waist region in opposed relationship with a front waist region of the garment shell, a back waist region in opposed relationship with a back waist region of the garment shell, and a crotch region extending longitudinally between and interconnecting the front and back waist regions of the absorbent assembly. The absorbent assembly is releasably attached generally at a front waist end thereof to the garment shell generally at the front waist end of the garment shell, and is also releasably attached generally at a back waist end thereof to the garment shell generally at the back waist end of the garment shell.

25 Claims, 12 Drawing Sheets

U.S. PATENT DOCUMENTS

| | | | |
|---|---|---|---|
| 2,842,129 A | 7/1958 | Ernstorff | |
| 2,859,752 A | 11/1958 | Haber | |
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,648,699 A | 3/1972 | Anderson et al. | |
| 3,678,516 A | 7/1972 | Backer | |
| 3,692,618 A | 9/1972 | Dorschner et al. | |
| 3,714,946 A | 2/1973 | Rudes | |
| 3,802,817 A | 4/1974 | Matsuki et al. | |
| 3,844,282 A | 10/1974 | King | |
| 3,849,241 A | 11/1974 | Butin et al. | |
| 3,859,667 A | 1/1975 | Roy | |
| 4,114,621 A | 9/1978 | Mims, Jr. | |
| 4,244,368 A | 1/1981 | Caradonna | |
| 4,280,230 A | 7/1981 | LaFleur | |
| 4,310,929 A | 1/1982 | Finlay | |
| 4,338,939 A | 7/1982 | Daville | |
| 4,340,563 A | 7/1982 | Appel et al. | |
| 4,555,245 A | 11/1985 | Armbruster | |
| 4,644,945 A | 2/1987 | Thorner | |
| 4,663,220 A | 5/1987 | Wisneski et al. | |
| 4,664,663 A | 5/1987 | Brier | |
| 4,671,793 A | 6/1987 | Hults et al. | |
| 4,704,116 A | 11/1987 | Enloe | |
| 4,745,636 A | 5/1988 | Lunt | |
| 4,870,958 A | 10/1989 | Webster | |
| 4,872,221 A | 10/1989 | Stone, III | |
| 4,892,598 A | 1/1990 | Stevens et al. | |
| 4,940,464 A | 7/1990 | Van Gompel et al. | |
| 4,955,880 A | 9/1990 | Rodriquez | |
| 4,964,860 A | 10/1990 | Gipson et al. | |
| 4,965,122 A | 10/1990 | Morman | |
| 4,981,747 A | 1/1991 | Morman | |
| 5,046,272 A | 9/1991 | Vogt et al. | |
| 5,052,058 A | 10/1991 | Mueller | |
| 5,067,178 A | 11/1991 | Katchka | |
| 5,103,505 A | 4/1992 | Llorens | |
| 5,104,116 A | 4/1992 | Pohjola | |
| 5,108,385 A | 4/1992 | Snyder | |
| 5,135,522 A | 8/1992 | Fahrenkrug et al. | |
| 5,210,882 A | 5/1993 | Moretz et al. | |
| 5,213,881 A | 5/1993 | Timmons et al. | |
| 5,217,782 A | 6/1993 | Moretz et al. | |
| 5,224,405 A | 7/1993 | Pohjola | |
| 5,226,992 A | 7/1993 | Morman | |
| D341,243 S | 11/1993 | Costella et al. | |
| 5,297,296 A | 3/1994 | Moretz et al. | |
| 5,303,424 A | 4/1994 | Cromartie | |
| 5,306,536 A | 4/1994 | Moretz et al. | |
| 5,315,716 A | 5/1994 | Baum | |
| 5,315,717 A | 5/1994 | Moretz et al. | |
| 5,336,545 A | 8/1994 | Morman | |
| 5,364,382 A | 11/1994 | Latimer et al. | |
| 5,370,634 A | 12/1994 | Ando et al. | |
| 5,379,462 A | 1/1995 | Morgan et al. | |
| 5,389,095 A | 2/1995 | Suzuki et al. | |
| H1440 H | 5/1995 | New et al. | |
| 5,435,014 A | 7/1995 | Moretz et al. | |
| 5,445,628 A | 8/1995 | Gipson et al. | |
| 5,486,166 A | 1/1996 | Bishop et al. | |
| 5,490,846 A | 2/1996 | Ellis et al. | |
| 5,549,593 A | 8/1996 | Ygge et al. | |
| D377,557 S | 1/1997 | Jagger | |
| 5,649,913 A | 7/1997 | Cohen | |
| D382,386 S | 8/1997 | Malone | |
| 5,669,902 A | 9/1997 | Sivilich | |
| 5,690,626 A | 11/1997 | Suzuki et al. | |
| 5,690,627 A | 11/1997 | Clear et al. | |
| 5,700,256 A | 12/1997 | Yamamoto et al. | |
| 5,718,003 A | 2/1998 | Gwinn | |
| 5,766,389 A | 6/1998 | Brandon et al. | |
| 5,790,983 A | 8/1998 | Rosch et al. | |
| 5,827,260 A | 10/1998 | Suzuki et al. | |
| 5,853,405 A | 12/1998 | Suprise | |
| 5,858,012 A | 1/1999 | Yamaki et al. | |
| 5,858,515 A | 1/1999 | Stokes et al. | |
| 5,876,394 A | 3/1999 | Rosch et al. | |
| 5,891,122 A | 4/1999 | Coates | |
| D408,964 S | 5/1999 | Hernandez | |
| 5,906,604 A | 5/1999 | Ronnberg et al. | |
| 5,953,754 A | 9/1999 | Rosch et al. | |
| 5,978,971 A | 11/1999 | Wald | |
| D417,940 S | 12/1999 | Coates et al. | |
| 6,009,558 A | 1/2000 | Rosch et al. | |
| 6,010,586 A | 1/2000 | Suprise | |
| 6,013,066 A | 1/2000 | Samuelsson | |
| 6,018,822 A | 2/2000 | Hernandez | |
| 6,098,557 A | 8/2000 | Couillard et al. | |
| 6,105,171 A | 8/2000 | Niedermeyer | |
| 6,108,823 A | 8/2000 | Danes | |
| 6,115,847 A * | 9/2000 | Rosch et al. | 2/238 |
| 6,142,983 A | 11/2000 | Suprise et al. | |
| 6,145,132 A | 11/2000 | Towner | |
| 6,149,637 A | 11/2000 | Allen et al. | |
| 6,168,585 B1 | 1/2001 | Cesco-Cancian | |
| 6,174,303 B1 | 1/2001 | Suprise et al. | |
| 6,192,521 B1 | 2/2001 | Alberts et al. | |
| 6,197,012 B1 | 3/2001 | Mishima et al. | |
| 6,293,934 B1 | 9/2001 | Kumasaka | |
| 6,293,936 B1 | 9/2001 | Otsubo | |
| 6,293,937 B2 | 9/2001 | Matsushita et al. | |
| 6,312,420 B1 | 11/2001 | Sasaki et al. | |
| 6,342,050 B1 | 1/2002 | Ronnberg et al. | |
| 6,358,350 B1 | 3/2002 | Glaug et al. | |
| 6,368,312 B1 | 4/2002 | Otsubo | |
| D456,995 S | 5/2002 | Baker | |
| 6,419,665 B1 | 7/2002 | Cohen | |
| 6,423,043 B1 | 7/2002 | Gustafsson | |
| 6,458,116 B1 | 10/2002 | Matsushita | |
| 6,475,201 B2 | 11/2002 | Saito et al. | |
| 6,487,727 B1 | 12/2002 | Harsant | |
| 6,500,163 B2 | 12/2002 | Ronnberg et al. | |
| 6,516,473 B2 | 2/2003 | Saito | |
| 6,539,554 B1 | 4/2003 | Portela | |
| 6,547,774 B2 | 4/2003 | Ono et al. | |
| 6,550,288 B2 | 4/2003 | Browder, Jr. et al. | |
| 6,558,364 B1 | 5/2003 | Santa Cruz et al. | |
| 6,585,840 B2 | 7/2003 | Rabe et al. | |
| 6,635,042 B2 | 10/2003 | Kumasaka | |
| 6,648,868 B2 | 11/2003 | Sayama et al. | |
| 6,666,851 B2 | 12/2003 | Otsubo et al. | |
| 6,761,712 B2 | 7/2004 | Otsubo et al. | |
| 2002/0035747 A1 | 3/2002 | Kusibojoska et al. | |
| 2002/0087137 A1* | 7/2002 | Christoffel et al. | 604/385.01 |
| 2002/0123732 A1 | 9/2002 | Koyama et al. | |
| 2003/0088955 A1 | 5/2003 | Bridges | |
| 2003/0115660 A1 | 6/2003 | Hopkins | |
| 2003/0217407 A1 | 11/2003 | Andrews-Jones | |
| 2003/0217803 A1 | 11/2003 | Hermansson et al. | |
| 2003/0229329 A1 | 12/2003 | Mercier et al. | |
| 2004/0060648 A1 | 4/2004 | Thorson et al. | |
| 2004/0082932 A1 | 4/2004 | Lauritzen | |
| 2004/0098791 A1 | 5/2004 | Faulks | |
| 2004/0102746 A1 | 5/2004 | Mortell et al. | |
| 2004/0107481 A1 | 6/2004 | Mortell et al. | |
| 2004/0116881 A1 | 6/2004 | Nordness et al. | |
| 2005/0125879 A1 | 6/2005 | Yang et al. | |
| 2005/0131377 A1 | 6/2005 | Franke et al. | |

| | | | |
|---|---|---|---|
| 2005/0131381 A1 | 6/2005 | Kuen et al. | |

FOREIGN PATENT DOCUMENTS

| | | |
|---|---|---|
| AT | 168478 | 6/1951 |
| AU | 94/80371 B | 4/1995 |
| DE | 435 579 | 2/1927 |
| DE | 435579 | 2/1927 |
| DE | 839 244 | 5/1952 |
| DE | 839244 | 5/1952 |
| EP | 1 342 022 | 12/1973 |
| EP | 0 217 032 | 7/1986 |
| EP | 0 400 895 A1 | 12/1990 |
| EP | 0 549 988 B1 | 12/1992 |
| EP | 0 763 353 A2 | 9/1996 |
| EP | 0 904 758 A2 | 3/1999 |
| EP | 0 911 006 A1 | 4/1999 |
| EP | 0 933 072 B1 | 8/1999 |
| EP | 1 108 373 A1 | 12/1999 |
| EP | 1 188 427 A1 | 5/2000 |
| EP | 1 048 231 A1 | 11/2000 |
| EP | 1 060 677 A1 | 12/2000 |
| EP | 1 125 571 A2 | 2/2001 |
| EP | 1 092 355 A1 | 4/2001 |
| EP | 1 108 371 A1 | 6/2001 |
| EP | 1 108 372 A1 | 6/2001 |
| EP | 1 166 730 A2 | 6/2001 |
| EP | 1 118 277 A1 | 7/2001 |
| EP | 1 159 883 A1 | 12/2001 |
| EP | 1 179 302 A2 | 2/2002 |
| EP | 1 184 012 A1 | 3/2002 |
| EP | 1 219 273 A2 | 7/2002 |
| EP | 1 247 506 A2 | 10/2002 |
| EP | 1 260 206 A2 | 11/2002 |
| EP | 1 504 738 A2 | 9/2005 |
| FR | 1276791 | 11/1961 |
| GB | 701081 | 12/1953 |
| GB | 0774712 A | 5/1957 |
| GB | 0774713 A | 5/1957 |
| GB | 2 196 525 A | 10/1986 |
| GB | 2 208 263 A | 3/1989 |
| GB | 2 269 978 A | 3/1994 |
| GB | 2 269 998 A | 3/1994 |
| GB | 2 269 999 A | 3/1994 |
| GB | 2 327 859 A | 2/1999 |
| JP | 2000355801 A | 12/2000 |
| JP | 2001-172802 A | 6/2001 |
| JP | 2001-204762 A | 7/2001 |
| JP | 2001-204764 A | 7/2001 |
| JP | 2001-204765 A | 7/2001 |
| JP | 2001-207301 A | 8/2001 |
| JP | 2001-245929 A | 9/2001 |
| JP | 2001-248002 A | 9/2001 |
| JP | 2001-254202 A | 9/2001 |
| JP | 2001238909 A2 | 9/2001 |
| JP | 2001-299813 A | 10/2001 |
| JP | 2001-309946 A | 11/2001 |
| JP | 2001-333932 A | 12/2001 |
| JP | 2002-035022 A | 2/2002 |
| WO | WO 95/16421 A1 | 6/1995 |
| WO | WO 95/18589 A1 | 7/1995 |
| WO | WO 96/03949 A1 | 2/1996 |
| WO | WO 96/03950 A1 | 2/1996 |
| WO | WO 97/24091 A1 | 7/1997 |
| WO | WO 98/53785 A1 | 12/1998 |
| WO | WO 99/33421 A1 | 7/1999 |
| WO | WO 00/37009 A2 | 6/2000 |
| WO | WO 01/58401 A1 | 8/2001 |
| WO | WO 01/61093 A1 | 8/2001 |
| WO | WO 01/67900 A1 | 9/2001 |
| WO | WO 01/88245 A2 | 11/2001 |
| WO | WO 02/067833 A1 | 9/2002 |
| WO | WO 2004/073430 A2 | 9/2004 |

OTHER PUBLICATIONS

International Search Report for PCT/US2004/021644 dated Nov. 25, 2004, 4 pages.
International Search Report for PCT/US2004/021613 dated Nov. 25, 2004, 4 pages.
US 5,915,536, 06/1999, Alberts et al. (withdrawn)

* cited by examiner

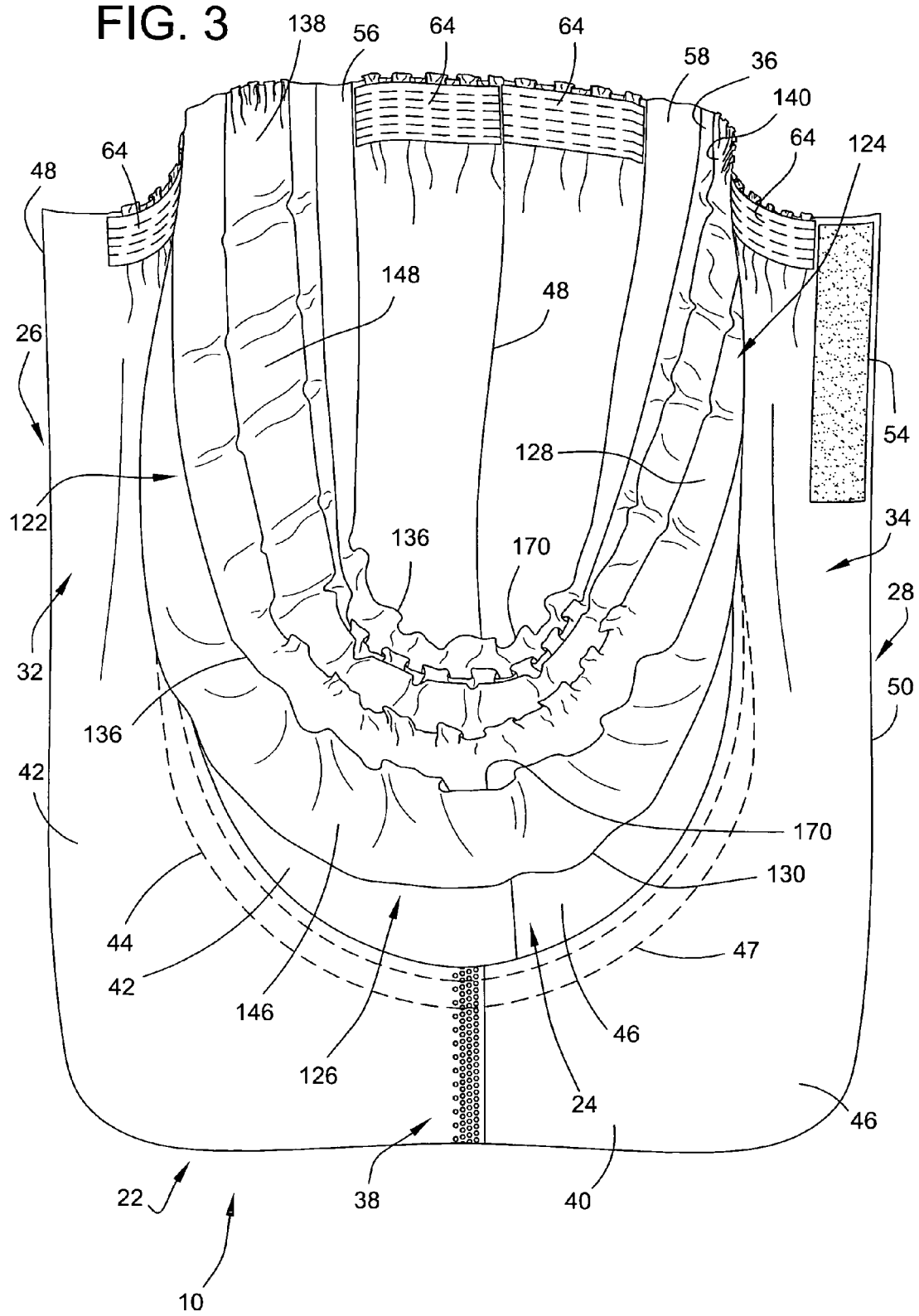

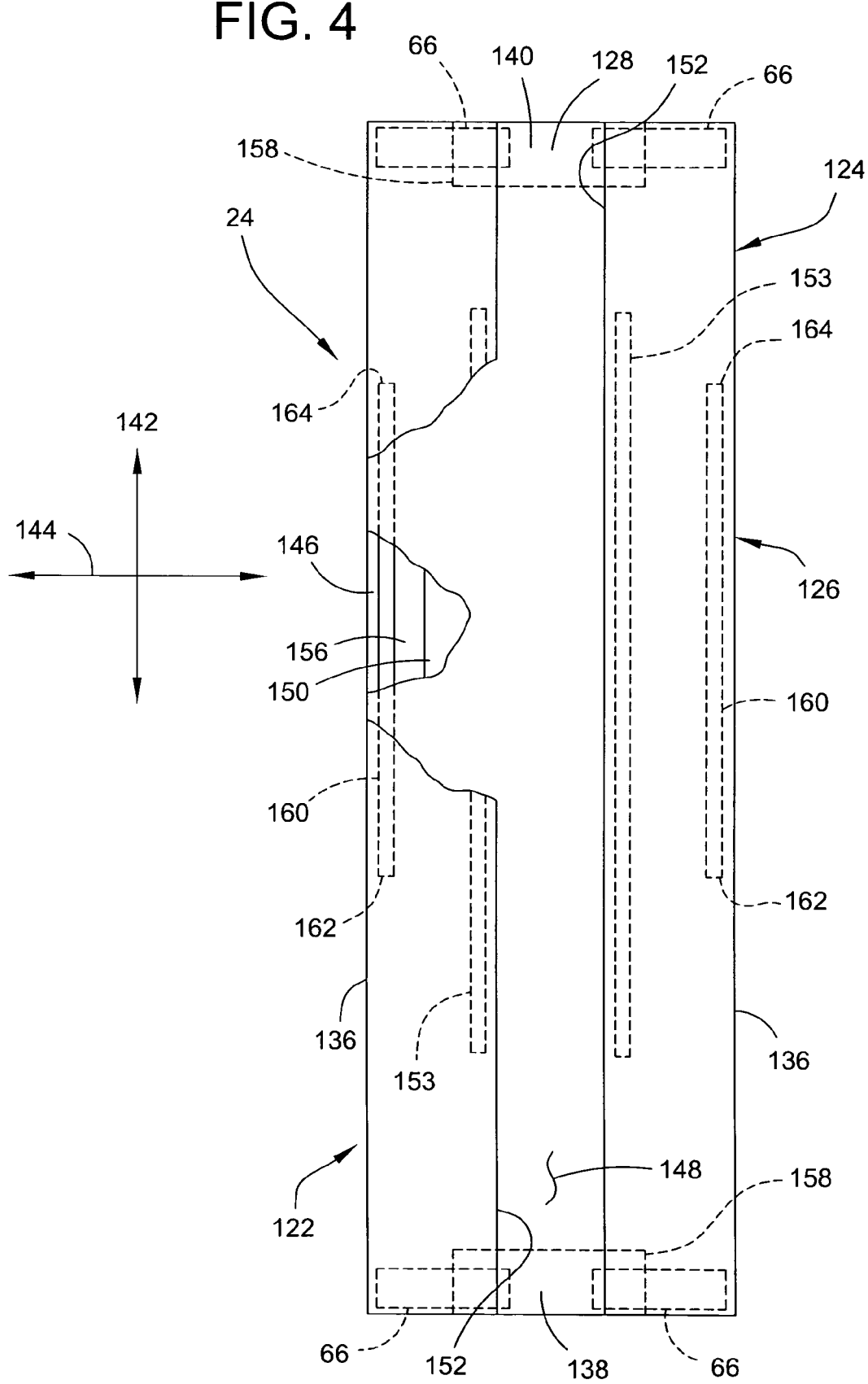

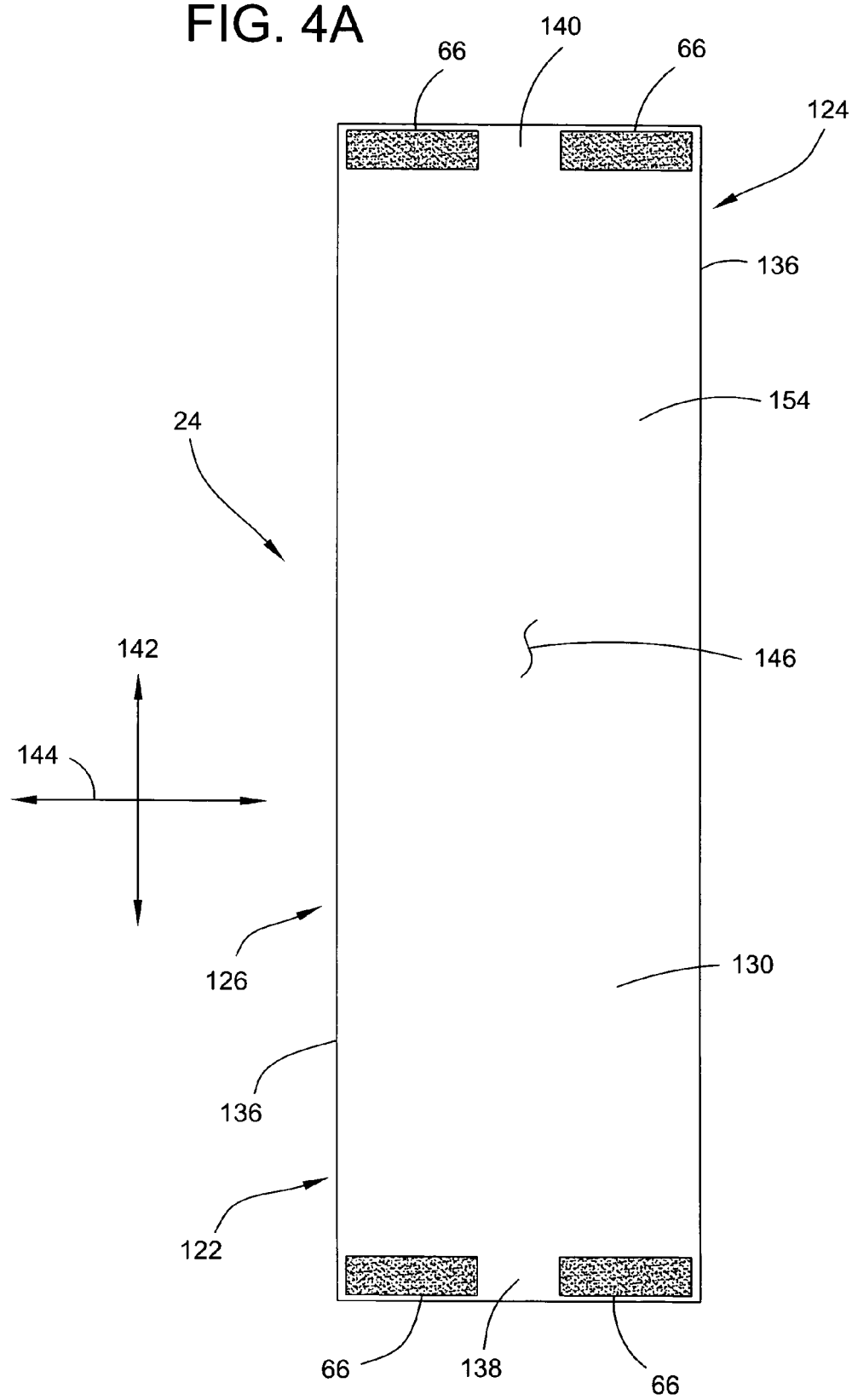

ABSORBENT GARMENT

BACKGROUND OF THE INVENTION

This invention relates generally to absorbent garments, and more particularly to such absorbent garments having the appearance of conventional clothing.

Personal wear garments and other articles find widespread use as personal care products including, without limitation, diapers, children's toilet training pants, adult incontinence garments, sanitary napkins and the like, as well as surgical bandages and sponges. The primary purpose of such articles is to take in and retain body exudates released by a wearer to thereby prevent soiling of the wearer's or caregiver's clothing. Certain absorbent articles are suitably disposable in that they are intended to be discarded after a limited period of use, i.e., the articles are not intended to be laundered or otherwise restored for reuse. Disposable absorbent articles typically comprise an absorbent body disposed between a liner, which contacts the wearer's skin, and an outer cover, which inhibits liquid body waste absorbed by the absorbent body from leaking out of the article. The liner of the absorbent article is typically liquid permeable to permit liquid body waste to pass therethrough for absorption by the absorbent body.

In particular absorbent articles, such as children's training pants, various attempts have been made to make the articles more visually appealing, such as by applying certain graphics or other features which make the articles appear more like conventional clothing, and more particularly like conventional undergarments. Training pants represent an intermediate stage for a child between using diapers and using cloth underpants. By making the training pants more closely resemble the undergarments or other clothing that an older sibling or parent wears, it is believed that children ready for toilet training will be more amenable to wearing the training pants. Other absorbent pants-type articles are worn by older children that still experience nighttime incontinence and by adults who experience periodic incontinence. These persons are typically more sensitive to issues of discretion and therefore desire some way to conceal the fact that they are wearing absorbent pants.

One drawback to simply improving the external appearance of existing absorbent pants is that the entire pants must still be discarded after use. As a result, additional features which are added to entice children to wear the pants or otherwise conceal the absorbent look of the pants add further costs to making and using the pants. Moreover, clothes must still be worn over the absorbent pants, which can be uncomfortable and results in a rather bulky appearance. Also, to inhibit the leakage of exudates from absorbent articles such as training pants or other absorbent pants, it is important that the article fit generally snug against the wearer's body. For example, conventional training pants are constructed to provide a generally elastical fit about the wearer's waist and about the wearer's legs to inhibit leakage from the pants. However, many conventional garments that are worn about one's waist, such as shorts, skirts, skorts, boxer shorts, swim trunks and the like, all have a more loose fitting appearance, particularly about the legs of the wearer.

SUMMARY OF THE INVENTION

In general, an absorbent garment according to one embodiment of the present invention for personal wear about the wearer's waist comprises a garment shell configured for encircling the wearer's waist and having a front waist region, a front waist end at the front waist region, a back waist region and a back waist end at the back waist region. An absorbent assembly is disposed within the garment shell and is constructed to take in and retain body exudates released by the wearer. The absorbent assembly has an inner surface adapted for contiguous relationship with the wearer's body, an outer surface, a front waist region in opposed relationship with the front waist region of the garment shell, and a back waist region in opposed relationship with the back waist region of the garment shell. The absorbent assembly also has a crotch region extending longitudinally between and interconnecting the front waist region of the absorbent assembly and the back waist region of the absorbent assembly, a front waist end and a back waist end. The absorbent assembly is releasably attached generally at its front waist end to the garment shell generally at the front waist end of the garment shell, and is also releasably attached generally at its back waist end to the garment shell generally at the back waist end of the garment shell.

DEFINITIONS

Within the context of this specification, each term or phrase below will include the following meaning or meanings.

"Attached" refers to the joining, adhering, connecting, bonding, or the like, of two or more elements.

"Hydrophilic" describes fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, and fibers having contact angles greater than 90 degrees are designated "nonwettable" or hydrophobic.

"Layer" when used in the singular can have the dual meaning of a single element or a plurality of elements.

"Liquid impermeable," when used in describing a layer or multi-layer laminate means that liquid body waste, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Longitudinal," and "transverse" or "lateral," have their customary meaning, as indicated by the longitudinal and transverse axes depicted in FIG. 4 and respectively designated 142 and 144. The longitudinal axis lies in the plane of the article and is generally parallel to a vertical plane that bisects a standing wearer into left and right body halves when the article is worn. The transverse or lateral axis lies in the plane of the article generally perpendicular to the longitudinal axis.

"Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameters. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

The term "microfibers" means small-diameter fibers having an average diameter not greater than about 100 microns, for example, having a diameter of from about 0.5 microns to about 50 microns, more specifically microfibers may also have an average diameter of from about 1 micron to about 20 microns. Microfibers having an average diameter of about 3 microns or less are commonly referred to as ultra-fine microfibers. A description of an exemplary process of making ultra-fine microfibers may be found in, for example, U.S. Pat. No. 5,213,881, entitled "A Nonwoven Web With Improved Barrier Properties".

"Non-woven" as used in reference to a material, web or fabric refers to such a material, web or fabric having a structure of individual fibers or threads that are interlaid, but not in a regular or identifiable manner as in a knitted fabric. Non-woven materials, fabrics or webs have been formed from many processes such as, for example, meltblowing processes, spunbonding processes, air laying processes, and bonded carded web processes. The basis weight of non-wovens is usually expressed in ounces of material per square yard (osy) or grams per square meter (gsm) and the fiber diameters are usually expressed in microns. (Note: to convert from osy to gsm, multiply osy by 33.91.).

"Operatively joined," with reference to the attachment of an elastic member to another element, means that the elastic member when attached to or connected to the element, or treated with heat or chemicals, by stretching, mechanical straining or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either direct, such as by joining the member directly to an element, or can be indirect, such as by means of another member disposed between the member and the element.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the article.

"Spunbonded fibers", or "spunbond fibers", means small-diameter fibers that are typically formed by extruding molten thermoplastic material as filaments from a plurality of fine capillaries of a spinneret having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al., each of which is incorporated by reference in its entirety and in a manner consistent with the present document. Spunbond fibers are quenched and generally not tacky when they are deposited onto a collecting surface. Spunbond fibers are generally continuous and often have average diameters larger than about 7 microns, and more particularly between about 10 and 30 microns. A spunbond material, layer, or substrate comprises spunbonded (or spunbond) fibers.

"Stretch bonded" refers to an elastic member being bonded to another member while the elastic member is extended at least about 25 percent of its relaxed length. More suitably, the term "stretch bonded" refers to the situation wherein the elastic member is extended at least about 100 percent, and even more suitably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Thermoplastic" describes a material which softens when exposed to heat and which substantially returns to a non-softened condition when cooled to room temperature.

These terms may be further defined with additional language in the remaining portions of the specification.

BRIEF DESCRIPTION OF THE DRAWINGS

FIG. 3 is a side elevation of the absorbent garment of FIG. 1 with a side seam of the absorbent garment shown in an unfastened condition;

FIG. 4 is a plan view of an absorbent assembly of the absorbent garment of FIG. 1 with the absorbent assembly shown in an unfastened, stretched and laid flat condition, and showing the surface of the absorbent assembly that faces the wearer of the absorbent garment, and with portions cut away to show underlying features;

FIG. 4a is a plan view similar to FIG. 4, but showing the surface of the absorbent that faces away from the wearer of the absorbent garment;

Corresponding reference characters indicate corresponding parts throughout the drawings.

DETAILED DESCRIPTION

Figure 1:
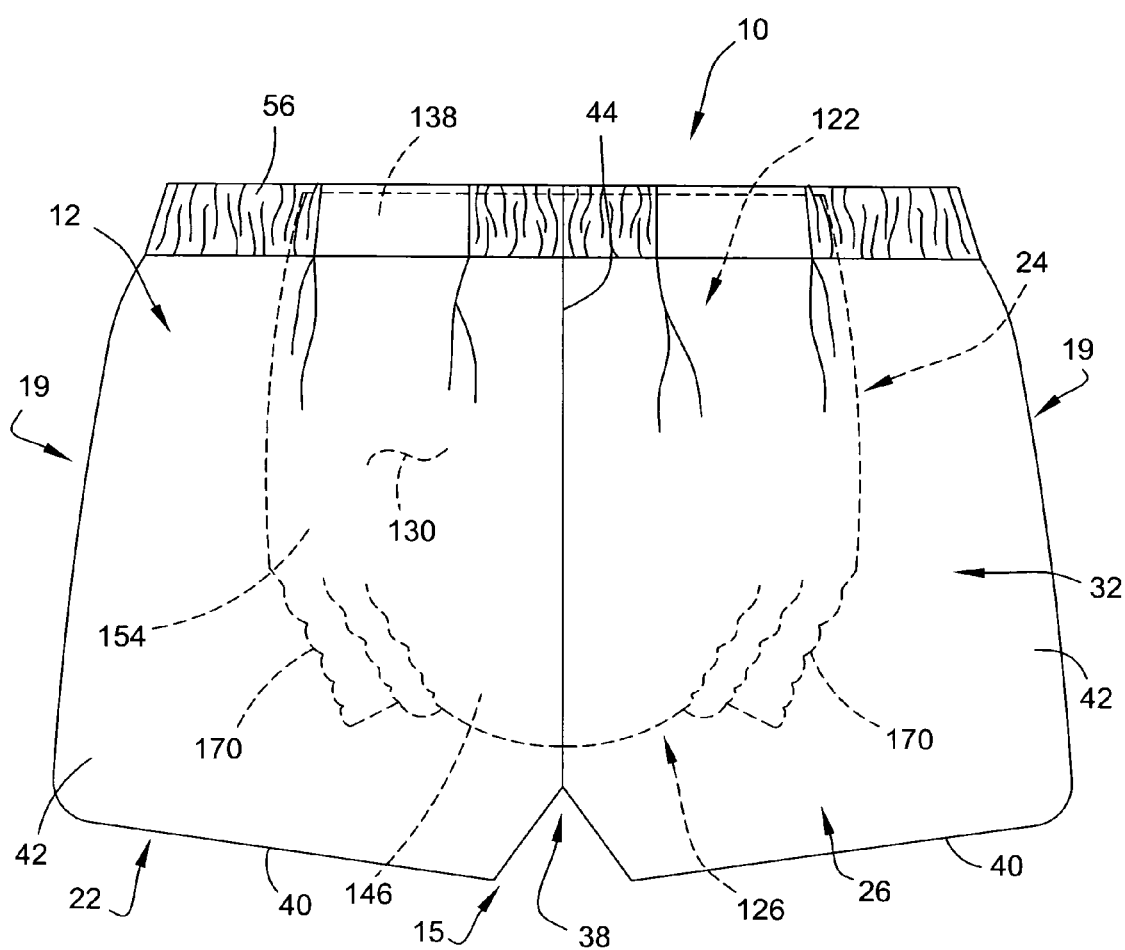
FIG. 1 is a front elevation of an absorbent garment according to one embodiment of the present invention.
Figure 2:
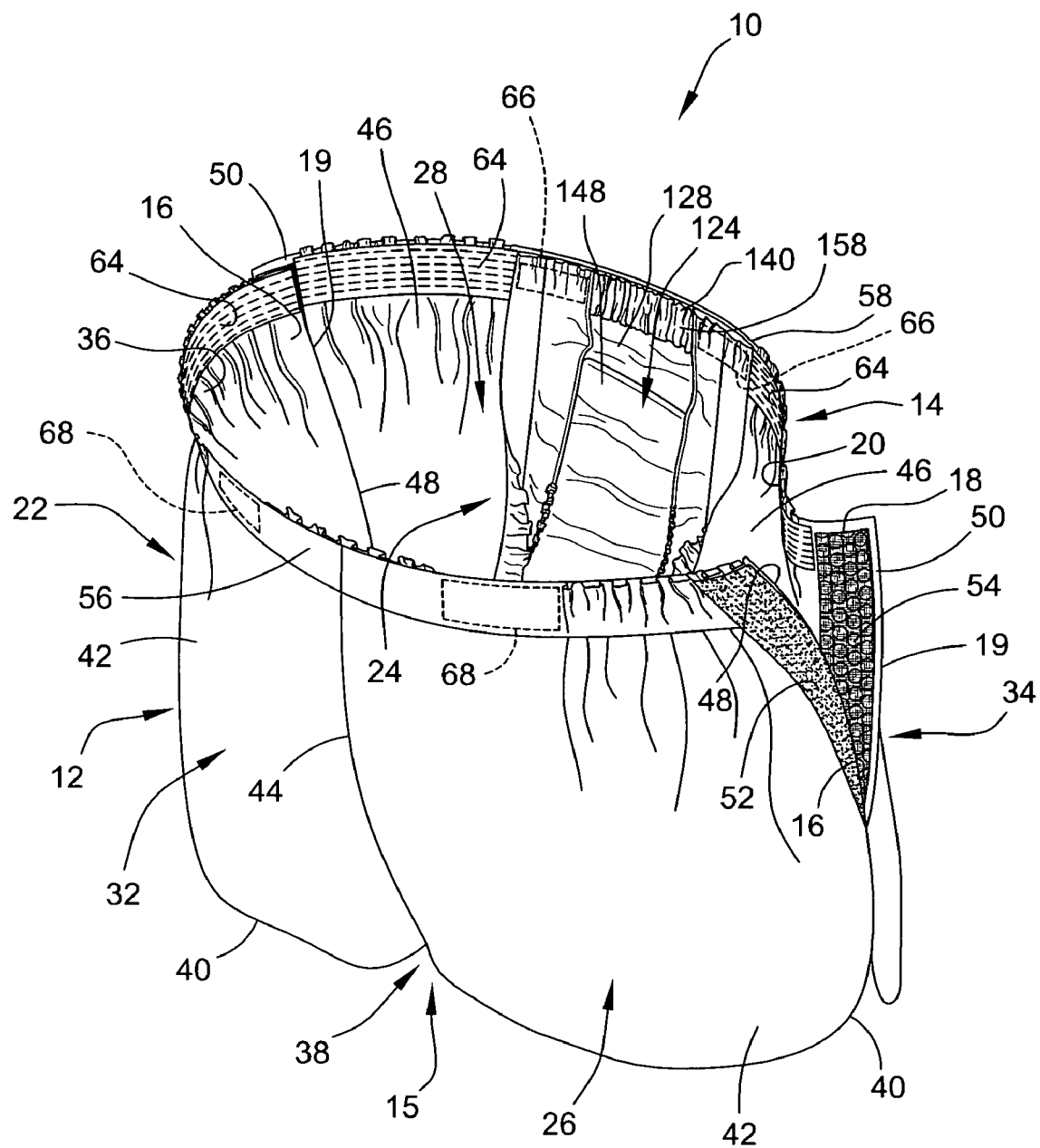
FIG. 2 is a perspective of the absorbent garment of FIG. 1 with a side seam of the absorbent garment shown in an unfastened condition.

Referring now to the drawings, and in particular to FIGS. 1 and 2, an absorbent garment according to one embodiment of the present invention is indicated in its entirety by the reference numeral 10. The absorbent garment 10 is configured to be worn on a wearer's waist and generally has a front waist region, indicated generally at 12, a back waist region, indicated generally at 14 and a crotch region, indicated generally at 15. The front and back waist regions 12, 14 have respective side margins 16, 18 which are attached to each other along side seams 19 of the garment to form a three dimensional configuration of the garment during wear and having a waist opening, generally indicated at 20. As used herein, the term "seam" is intended to refer to a region along which two components are overlapped or otherwise in abutment with each other and may or may not be attached to each other.

As described further herein, the absorbent garment is suitably configured to resemble conventional clothing such as shorts (e.g., boxer shorts, gym shorts, running shorts, etc.), skirts, skorts (i.e., a combination of a skirt and a pair of shorts), swim trunks and the like, while providing the functions of conventional absorbent articles, such as taking in and retaining body exudates released by the wearer. The absorbent garment 10 comprises a garment shell, generally indicated at 22 and constructed to provide the desired resemblance of the garment to conventional clothing, and an absorbent assembly, generally indicated at 24, disposed within and releasably attached to the garment shell and constructed to take in and retain body exudates released by the wearer.

With particular reference to FIGS. 1 and 2, the garment shell 22 comprises a front panel assembly, which is generally indicated at 26, having laterally opposite side margins 48 and a back panel assembly, which is generally indicated at 28 in FIG. 2, having laterally opposite side margins 50. In the illustrated embodiment, the side margins 48 of the front panel assembly 26 broadly define the front side margins 16 of the absorbent garment 10 and the side margins 50 of the back panel assembly 28 broadly define the back side margins 18 of the absorbent garment. As will be described in further detail later herein, the side margins 48, 50 of the front and back panel assemblies 26, 28 of the garment shell 22 are overlapped and attached to each other to broadly define the side seams 19 of the absorbent garment 10, and to define the three-dimensional configuration of the garment shell during wear.

In its three-dimensional configuration as shown in FIGS. 1 and 2, the garment shell 22 has a front waist region 32 which at least in part defines the front waist region 12 of the absorbent garment 10, a back waist region 34 which at least in part defines the back waist region 14 of the absorbent garment, and front and back waist ends, designated 56 and 58, respectively, which together generally define a waist opening 36 of the garment shell. In the illustrated embodiment, the garment shell 22 is configured to resemble a pair of shorts and thus further has a crotch region 38 extending longitudinally between and interconnecting the front waist region 32 and the back waist region 34 of the garment shell. The crotch region 38 of the garment shell 22 at least in part defines the crotch region 15 of the absorbent garment 10, and also in part defines leg openings 40 of the garment shell (broadly referred to herein as outer leg openings of the absorbent garment). However, it is understood that the crotch region 38 of the garment shell 22 may be omitted (so that the crotch region 15 of the absorbent garment 10 is defined solely by the absorbent assembly 24 as described later herein), such as where the garment shell is intended to resemble a skirt (in which case only one leg opening 40 of the garment shell is provided to accommodate both legs of the wearer), without departing from the scope of this invention.

The front panel assembly 26 of the garment shell 22 comprises a pair of panel members 42 which are permanently attached to each other, such as by ultrasonic bonding, thermal bonding, adhesive bonding, stitching or other conventional attachment technique, along a central seam 44 extending longitudinally from the front waist region 32 to the crotch region 38 of the garment shell. The back panel assembly 28 comprises a pair of panel members 46 configured and permanently attached to each other in a manner similar to the panel members 42 of the front panel assembly 26 along a central seam 47 (FIG. 3) extending longitudinally from the back waist region 34 to the crotch region 38 of the garment shell 22. It is understood, however, that each of the front and back panel assemblies 26, 28 may be constructed of a single panel member (e.g., of unitary construction) without departing from the scope of this invention. Alternatively, the front and back panel members 42, 46 on one side of the garment shell 22 may be formed integrally at the crotch region 38 thereof so that no attachment of the panel members is necessary at the leg openings The panel members 42, 46 of the front and back panel assemblies 26, 28 of the garment shell 22 can be constructed of any suitable material, and more suitably a material that provides a generally cloth-like texture. The panel members 42, 46 are also suitably constructed of a material which is relatively durable so that the garment shell 22 can be re-used through multiple replacements of the absorbent assembly. It is also contemplated that the panel members 42, 46 may, but need not necessarily be, constructed of a material suitable for laundering to permit laundering of the garment shell. As an example, the panel members 42, 46 may be constructed from natural and/or synthetic sources and may be constructed in any suitable manner including, but not limited to nonwovens such as spunbond, meltblown, spunbond film laminates, bonded carded web, spunlace, hydroentangled, and needlepunched; knit fabrics such as stretch knit, fleece knit, herringbone knit, jersey knit, raschel knit; and woven fabrics such as broadcloth, twill, percale, poplin, muslin, cambric, chino, flannel, silks and woolens. The panel members 42, 46 are suitably liquid permeable, although it is understood that the panel members may be liquid impermeable without departing from the scope of this invention.

With particular reference to FIGS. 2 and 3, the front and back panel assemblies 26, 28 of the garment shell 22 can be releasably attached to each other at the respective side margins 48, 50 of the panel assemblies. For example, in the illustrated embodiment a fastening component 52 is attached to each side margin 48 of the front panel assembly 26 and is adapted for refastenable engagement with a complementary fastening component 54 attached to each respective side margin 50 of the back panel assembly 28. Although the garment shell 22 as illustrated in FIG. 2 has the side margins 50 of the back panel assembly 28 overlapping the side margins 48 of the front panel assembly 26 upon releasable attachment, the garment shell can instead be configured so that the side margins of the front panel assembly overlap the side margins of the back panel assembly for releasable attachment.

The fastening components 52, 54 can comprise any refastenable fasteners suitable for garments, such as adhesive fasteners, cohesive fasteners, mechanical fasteners, or the like. In particularly suitable embodiments the fastening components 52, 54 comprise mechanical fastening elements provided by interlocking geometric shaped materials such as hooks, loops, bulbs, mushrooms, arrowheads, balls on stems, male and female mating components, buckles, snaps, or the like. For example, in the illustrated embodiment the fastening components 52 comprise hook fasteners and the fastening components 54 comprise complementary loop fasteners arrayed so that the hook fasteners face generally away from the wearer. Alternatively, the fastening components 52 may comprise loop fasteners and the fastening components 54 may comprise complementary hook fasteners. One skilled in the art will recognize that the shape, density and polymer composition of the hooks and loops may be selected to obtain the desired level of engagement between the fastening components 52, 54. A more aggressive hook material may comprise a material with a greater average hook height and/or a greater percentage of directionally-aligned hooks. It is also contemplated that the fastening components 52, 54 can comprise interlocking similar surface fasteners, or adhesive and cohesive fastening elements such as an adhesive fastener and an adhesive-receptive landing zone or material; or the like.

Loop fastener as used herein refers to a fabric or material including a plurality of loop members. The loop material can be formed of any suitable material, such as acrylic, polyamide, polyethylene, polypropylene or polyester, and can be formed by methods such as warp knitting, stitch bonding or needle punching. Loop materials can also comprise any fibrous structure capable of entangling or catching hook materials, such as carded, spunbonded or other nonwoven webs or composites, including elastomeric and nonelastomeric composites. Suitable loop materials are available from Guilford Mills, Inc., Greensboro, N.C., U.S.A. under the trade designation No. 36549. Another suitable loop material can comprise a pattern un-bonded web as disclosed in co-assigned U.S. Pat. No. 5,858,515 issued Jan. 12, 1999 to Stokes, et al., which is incorporated herein by reference.

The loop material may be attached to a base, or backing structure, and the composite then attached to the particular component of the absorbent garment 10, such as the front or back panel assemblies 26, 28 of the garment shell 22, or the loop material may be attached directly to the absorbent garment component so that the component (e.g., the garment shell) serves as a backing for the loop material, or the loop material may be formed integrally with the component (e.g., the garment shell), such as by constructing one or more layers or surfaces of the component to comprise a loop material.

Hook fastener as used herein refers to a fabric or material having a base or backing structure and a plurality of hook members extending upwardly from at least one surface of the backing structure. It should be understood that the term "hook" as used in reference to the hook members is non-limiting in the sense that the engaging elements of the hook fasteners may comprise shapes such as hooks, "T's", "mushrooms" or any other shape so long as they are adapted to releasably engage the loop fasteners so as to provide a secure, but non-destructive releasable attachment. It is understood that the attachment may be of limited lifetime, e.g., gradual degradation of the attachment may occur with repeated engagements and disengagements.

In contrast to the loop fasteners which suitably comprise a flexible fabric, the hook material may advantageously comprise a resilient material to minimize unintentional disengagement of the fastening components 52, 54 as a result of the hook material becoming deformed and catching on clothing or other items. The term "resilient" as used in reference to the hook fasteners refers to an interlocking material having a predetermined shape and the property of the interlocking material to resume the predetermined shape after being engaged and disengaged from a mating, complementary interlocking material.

Suitable hook material can be molded or extruded from nylon, polypropylene, polyethylene or another suitable material. Suitable single-sided hook materials for the fastening components 52, 54 as well as other fastening components described later herein are available from commercial vendors such as Velcro Industries B.V., Amsterdam, Netherlands or affiliates thereof, identified as Velcro HTH-829, which has a thickness of about 0.9 millimeters (35 mils) and HTH-851, which has a thickness of about 0.5 millimeters (20 mils); and Minnesota Mining & Manufacturing Co., St. Paul, Minn. U.S.A., including specific materials identified as CS-600. As with the loop fastener, it is understood that the hook material may be formed integrally with a component of the absorbent garment 10, such as the garment shell 22 in the instance of the fastening components 52, 54, without departing from the scope of this invention.

The fastening components 52, 54 are shown in FIGS. 2 and 3 as having a generally rectangular shape, although they may instead be square, round, oval, curved or other suitable shapes. The fastening components 52, 54 extend along the respective side margins 48, 50 of the front and back panel assemblies 26, 28 generally from the waist ends 56, 58 of the panel assemblies to a position intermediate the waist ends and the leg openings 40 of the garment shell so that the absorbent garment side margins 16, 18 are releasably attached to each other along upper segments of the side seams 19. As an example, the fastening components 52, 54 suitably extend from the front and back waist ends 56, 58 of the garment shell 22 along the side margins 48, 50 thereof in the range of about 25 percent to about 50 percent of the length of the side margins (broadly, about 25 percent to about 50 percent of the length of the side seams 19 of the absorbent garment 10). However, it is understood that the fastening components 52, 54 may be longer or shorter without departing from the scope of this invention. Thus, in the illustrated embodiment, only a portion of the side seams 19 of the absorbent garment are refastenable.

The segment of the garment shell 22 along which the side margins 48, 50 are not releasably attached (e.g., extending from the bottom of the fastening components 52, 54 to the leg openings 40 of the garment shell) are suitably free from any form of attachment. In such an embodiment, the non-refastenable portion of the side seams 19 of the absorbent garment 10 are referred to as being open and the side margins 16, 18 thereof are referred to as being unattached. Alternatively, the side margins 48, 50 of the front and back assemblies 26, 28 of the garment shell 22 may be non-refastenably (e.g., frangibly or permanently) attached to each other along the portion of side margins extending from the bottom of the fastening components to the leg openings 40, such as by adhesive, or by thermal or ultrasonic bonding, or by other suitable attachment techniques.

It is also contemplated that the fastening components 52, 54 may instead extend from the leg openings 40 of the garment shell partially up along the side margins 48, 50 of the front and back panel assemblies 26, 28 (e.g., so that only a lower segment of the side seams 19 of the absorbent garment are refastenable). The side margins 48, 50 extending from the tops of the fastening components 52, 54 to the waist ends 56, 58 of the garment shell 22 may be non-refastenably (e.g., frangibly or permanently) attached to each other in the manner described previously. In other embodiments, the fastening components 52, 54 may extend the entire length of the side margins 48, 50 of the front and back panel assemblies 26, 28 of the garment shell 22 (e.g., such that the side seams 19 of the absorbent garment 10 are refastenable along their full length). Also, while the fastening components 52, 54 are illustrated as being continuous along each respective side margin 48, 50, it is understood that two or more fastening components may be attached to each respective side margin in spaced relationship along the side margin without departing from the scope of this invention.

It is further contemplated that the side margins 48, 50 of the garment shell 22 may instead be permanently or frangibly (e.g., non-refastenably) attached along all or part of the full length thereof whereby no portions of the side margins are refastenable. It is also understood that the the garment shell 22 may be formed to omit the side margins 48, 50 thereof, such as by integrally forming the respective front and back panel members 42, 46 on each side of the shell.

The amount of overlap between the side margins 48, 50 of the front and back panel assemblies 26, 28 at the side seams 19 of the garment shell 22 (broadly, the overlap of the side margins 16, 18 of the front and back waist regions 12, 14 of the absorbent garment 10) is suitably in the range of about 0.1 inches (2.5 millimeters (mm)) to about 6 inches (152.4 mm), and more suitably in the range of about 0.5 (12.7 mm) inches to about 3 inches (76.2 mm). It is contemplated that the fastening components 52, 54 on at least one of the front and back panel assemblies 26, 28 may have a width corresponding to the range of overlap to permit a variable fit of the absorbent garment over a relatively wide range of wearer sizes.

The fastening components 52, 54 are suitably attached to the respective front and back panel assemblies 26, 28 by mechanical bonding. As used herein, mechanical bonding refers to non-adhesive bonding, such as by the application of pressure, ultrasonic energy, heat, laser energy or any other suitable form of energy which joins the fastening components to the panel assemblies 26, 28. Alternatively, or additionally, the fastening components 52, 54 may be adhered, such as by adhesive or cohesive means, to the respective front and back panel assemblies 26, 28. It is also contemplated that the fastening components 52, 54 may be formed integrally with the respective front and back panel assemblies 26, 28 and remain within the scope of this invention.

In addition to the front and back panel assemblies 26, 28 of the garment shell 22 being releasably attached to each other at the respective side margins 48, 50 thereof, or as an alternative thereto, it is contemplated that the panel assemblies may be releasably attached to each other at the crotch region 38 of the garment shell to allow the garment shell to be unfastened at the crotch region and pulled up relative to the absorbent assembly 24 for inspecting or otherwise replacing the absorbent assembly. For example, fastening components (not shown in FIGS. 2-4 but indicated at 60, 62 in FIG. 8) may be attached to the front and back panel assemblies 26, 28 of the garment shell 22 generally at the crotch region 38 thereof to permit releasable attachment of the panel assemblies at the crotch region.

To further enhance the appearance of the absorbent garment 10 as well as the fit of the absorbent garment on the wearer's waist, elastic members 64 (e.g., waistband elastics) are operatively joined to the front and back panel assemblies 26, 28 generally at the respective waist ends 56, 58 thereof. For example, as best seen in FIGS. 2 and 3, two elastic members 64 are operatively joined to the front waist end 56 of the garment shell 22 on laterally opposite sides of the absorbent assembly 24. Two more elastic members 64 are operatively joined to the back waist end 58, also on laterally opposite sides of the absorbent assembly 24. The elastic members 64 can be operatively joined to the garment shell 22 while in a stretched condition so that upon retraction the elastic members gather the garment shell at the front and back waist ends 56, 58 to provide a gathered appearance and to further provide an elastic fit of the absorbent garment on the wearer's waist. Alternatively, it is contemplated that a single elastic member (not shown) may be attached to each waist end 56, 58 of the garment shell 22 and extend laterally across all or only a portion of the width of the respective waist end without departing from the scope of this invention.

With further reference to FIGS. 2-6, the absorbent assembly 24 comprises a front waist region 122, a back waist region 124, a crotch region 126 interconnecting the front and back waist regions, an inner surface 128 configured for contiguous relationship with the wearer, and an outer surface 130 opposite the inner surface. The front waist region 122 comprises the portion of the absorbent assembly which, when the absorbent garment 10 is worn, is positioned on the front of the wearer while the back waist region 124 comprises the portion of the absorbent assembly which is positioned on the back of the wearer. The crotch region 126 of the absorbent assembly 24 comprises the portion of the assembly which is positioned between the legs of the wearer and covers the lower torso of the wearer. With additional reference to FIG. 4, the absorbent assembly 24 also has laterally opposite side edges 136 and longitudinally opposite waist ends, respectively designated herein as front waist end 138 and back waist end 140.

The absorbent assembly 24 is suitably "disposable," which as used herein refers to articles that are intended to be discarded after a limited period of use instead of being laundered or otherwise restored for reuse. However, it is contemplated that the absorbent assembly may be re-useable and remain within the scope of this invention. By way of illustration only, various materials and methods for constructing the absorbent assembly 24 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference.

The absorbent assembly 24 is illustrated in FIGS. 4 and 4a detached from the garment shell 22 and in a laid flat configuration. The absorbent assembly 24 is suitably rectangular in shape and has a longitudinal axis 142 and a transverse, or lateral axis 144. It is understood that the absorbent assembly 24 may be other than rectangular, such as hourglass-shaped, T-shaped, I-shaped or other suitable shape without departing from the scope of this invention. The absorbent assembly 24 comprises an outer cover 146 (FIG. 3), a bodyside liner 148 (FIG. 4) in superposed relationship with the outer cover, an absorbent body 150 disposed between the outer cover and the bodyside liner, and a pair of laterally spaced containment flaps 152 configured to inhibit the transverse flow of body exudates on the liner to the side edges 136 of the absorbent assembly.

The outer cover 146 of the absorbent assembly 24 suitably comprises a material which is substantially liquid impermeable, and may be stretchable or non-stretchable. As used herein, the term "stretchable" refers to a material that may be extensible or elastic. That is, the material may be extended, deformed or the like, without breaking, and may or may not significantly retract after removal of an extending force. As used herein, the term "elastic" refers to that property of a material where upon removal of an elongating force, the material is capable of recovering to substantially its unstretched size and shape or the material exhibits a significant retractive force. The term "extensible" refers to that property of a material where upon removal of an elongating force, the material experiences a substantially permanent deformation or the material does not exhibit a significant retractive force.

More suitably, the outer cover 146 comprises a multi-layered laminate structure in which at least one of the layers is liquid impermeable. For instance, the outer cover 146 can include a liquid permeable outer layer 154 and a liquid impermeable inner layer 156 (FIG. 4) which are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J. U.S.A. The liquid permeable outer layer 154 can be any suitable material and is desirably one that provides a generally cloth-like texture. One example of such a material is a 20 gsm (grams per square meter) spunbond polypropylene nonwoven web. The outer layer 154 may also be made of those materials described later herein from which the liquid permeable bodyside liner 148 is made.

The inner layer 156 of the outer cover 146 can be both liquid and vapor impermeable, or it may be liquid impermeable and vapor permeable. The inner layer 156 can be manufactured from a thin plastic film, although other flexible liquid impermeable materials may also be used. The liquid impermeable inner layer 156 prevents waste material from wetting articles, such as bed sheets and clothing, as well as the wearer and caregiver. A suitable liquid impermeable film for use as a liquid impermeable inner layer 156 of the outer cover 146 is a 0.02 millimeter polyethylene film commercially available from Pliant Corporation of Schaumburg, Ill., U.S.A.

Alternatively, the outer cover 146 may comprise a single layer of liquid impermeable material. As earlier mentioned, the liquid impermeable material can permit vapors to escape from the interior of the disposable absorbent article, while still preventing liquids from passing through the outer cover 146. For example, the outer cover 146 may be constructed of a microporous polymer film or a nonwoven fabric that has been coated or otherwise treated to impart a desired level of liquid impermeability. One such microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A. The single layer outer cover 146 may also be embossed and/or matte finished to provide a more cloth-like appearance.

The liquid permeable bodyside liner 148 is illustrated as overlying the outer cover 146 and absorbent body 150, and may but need not have the same dimensions as the outer cover 146. The bodyside liner 148 is desirably compliant, soft feeling, and non-irritating to the child's skin. Further, the bodyside liner 148 can be less hydrophilic than the absorbent body 150, to present a relatively dry surface to the wearer and to permit liquid to readily penetrate through the liner. Alternatively, the bodyside liner 148 can be more hydrophilic or can have essentially the same affinity for moisture as the absorbent body 150 to present a relatively wet surface to the wearer to increase the sensation of being wet. This wet sensation can be useful as a training aid. The hydrophilic/hydrophobic properties can be varied across the length, width and depth of the bodyside liner 148 and absorbent body 150 to achieve the desired wetness sensation or leakage performance.

The bodyside liner 148 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 148. For example, the bodyside liner 148 can be composed of a meltblown or spunbonded web of polyolefin fibers. The bodyside liner can also be a bonded-carded web composed of natural and/or synthetic fibers. The bodyside liner 148 can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C., U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire bodyside liner 148 or can be selectively applied to particular sections of the bodyside liner, such as the medial section along the longitudinal center line.

One example of a suitable liquid permeable bodyside liner 148 is a nonwoven bicomponent web having a basis weight of about 27 gsm. The nonwoven bicomponent web can be a spunbond bicomponent web, or a bonded carded bicomponent web. Suitable bicomponent fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like.

The absorbent body 150 (FIG. 4) is positioned between the outer cover 146 and the bodyside liner 148, which can be joined together by any suitable means such as adhesives, ultrasonic bonds, thermal bonds, or the like. The absorbent body 150 can be any structure which is generally compressible, conformable, non-irritating to the child's skin, and capable of absorbing and retaining liquids and certain body wastes, and may be manufactured in a wide variety of sizes and shapes, and from a wide variety of liquid absorbent materials commonly used in the art. For example, the absorbent body 150 can suitably comprise a matrix of hydrophilic fibers, such as a web of cellulosic fluff, mixed with particles of a high-absorbency material commonly known as superabsorbent material. In a particular embodiment, the absorbent body 150 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent body 150 to better contain and absorb body exudates. The concentration of the superabsorbent particles can also vary through the thickness of the absorbent body 150. Alternatively, the absorbent body 150 can comprise a laminate of fibrous webs and superabsorbent material, a foam or other suitable web construction.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 10 times its weight in water, and suitably is capable of absorbing more than about 25 times its weight in water.

In one embodiment, the absorbent body 150 comprises a blend of wood pulp fluff and superabsorbent material. One suitable type of pulp is identified with the trade designation CR1654, available from U.S. Alliance, Childersburg, Ala., U.S.A., and is a bleached, highly absorbent sulfate wood pulp containing primarily soft wood fibers and about 16 percent hardwood fibers. In general, the superabsorbent material is present in the absorbent body 150 in an amount of from 0 to about 90 weight percent based on total weight of the absorbent assembly. The absorbent body 150 may or may not be wrapped or encompassed by a suitable tissue wrap that aids in maintaining the integrity and/or shape of the absorbent assembly during use.

The containment flaps 152 are located generally adjacent to the side edges 136 of the absorbent assembly 24, and can extend longitudinally along the entire length of the absorbent assembly 24 as shown in FIG. 4 or only partially along the length of the absorbent assembly. Flap elastic members 153 (FIG. 4) are operatively joined with the containment flaps 152 in a suitable manner as is well known in the art, such as by adhering the elastic members to the flaps while the elastic members are in a stretched condition so that the flaps are biased by the elastic members to a longitudinally gathered configuration. The elasticized containment flaps 152 also define a partially unattached distal edge (e.g., unattached to the liner 148) which assumes an upright configuration in at least the crotch region 126 of the absorbent assembly 24 during wear to form a seal (e.g., an elastic fit) against the wearer's body. Suitable constructions and arrangements for the containment flaps 152 are generally well known to those skilled in the art and are described in U.S. Pat. No. 4,704,116 issued Nov. 3, 1987 to Enloe, which is incorporated herein by reference. It is understood, however, that the containment flaps 152 may be omitted without departing from the scope of this invention.

To further enhance the fit of the absorbent garment 10 on the wearer and to further inhibit leakage of body exudates, the absorbent assembly can also have waist elastic members 158 (FIGS. 2 and 4) and leg elastic members 160 (FIG. 4), as are known to those skilled in the art. The waist elastic members 158 can be operatively joined to the absorbent assembly 24 at the waist ends 138 and 140, such as by attaching the elastic members to the outer cover 146 and/or the bodyside liner 148 while the elastic members are in a stretched condition, so that upon retraction the elastic members gather the absorbent assembly at the waist ends to provide an elastic fit against the wearer's waist. In the illustrated embodiment the elastic members 158 which are operatively joined to the absorbent assembly 24, and the elastic members 64 which are operatively joined to the garment shell 22 on laterally opposite sides of the absorbent assembly, together provide an elastic fit of the absorbent garment 10 against substantially the entire waist of the wearer. The elastic members 158 are shown in FIG. 4 as extending only partially across the respective front and back waist ends 138, 140 of the absorbent assembly 24. It is understood, however, that the elastic members 158 may extend laterally across the full width of the absorbent assembly 24 at one or both waist ends 138, 140 without departing from the scope of this invention.

The leg elastic members 160 can be operatively joined to the outer cover 146 and/or the bodyside liner 148 and extend longitudinally adjacent the opposite side edges 136 generally through the crotch region 126 of the absorbent assembly 24. Each leg elastic member 160 has a front terminal point 162 and a back terminal point 164, which represent the longitudinal ends of the elastic gathering caused by the leg elastic members.

The flap elastic members 153, the waist elastic members 158 (as well as the elastic members 64 operatively joined with the garment shell 22), and the leg elastic members 160 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate.

The absorbent assembly 24 can also incorporate other materials or components designed primarily to receive, temporarily store, and/or transport liquid along the mutually facing surface with the absorbent body 150, thereby maximizing the absorbent capacity of the absorbent assembly. For example, one suitable additional component is commonly referred to as a surge layer (not shown). Surge layers are generally well known in the art as being constructed to quickly collect and temporarily hold liquid surges, and to transport the temporarily held liquid to the absorbent body 150.

Various woven and non-woven fabrics can be used to construct the surge layer. For example, the surge layer may be a layer made of a meltblown or spunbond web of synthetic fibers, such as polyolefin fibers. The surge layer may also be a bonded-carded-web or an airlaid web composed of natural and synthetic fibers. The bonded-carded-web may, for example, be a thermally bonded web that is bonded using low melt binder fibers, powder or adhesive. The webs can optionally include a mixture of different fibers. The surge layer may be composed of a substantially hydrophobic material, and the hydrophobic material may optionally be treated with a surfactant or otherwise processed to impart a desired level of wettability and hydrophilicity.

Examples of materials suitable for the surge layer are set forth in U.S. Pat. No. 5,486,166 issued Jan. 23, 1996 in the name of C. Ellis et al. and entitled "FIBROUS NONWOVEN WEB SURGE LAYER FOR PERSONAL CARE ABSORBENT ARTICLES AND THE LIKE"; U.S. Pat. No. 5,490,846 issued Feb. 13, 1996 in the name of Ellis et al. and entitled "IMPROVED SURGE MANAGEMENT FIBROUS NONWOVEN WEB FOR PERSONAL CARE ABSORBENT ARTICLES AND THE LIKE"; and U.S. Pat. No. 5,364,382 issued Nov. 15, 1994 in the name of Latimer et al. and entitled "ABSORBENT STRUCTURE HAVING IMPROVED FLUID SURGE MANAGEMENT AND PRODUCT INCORPORATING SAME", the disclosures of which are hereby incorporated by reference in a manner consistent with the present document.

With particular reference to FIGS. 2-4a, the absorbent assembly 24 is releasably attached to the garment shell 22 to permit detachment and replacement of the absorbent assembly (or detachment and laundering thereof where the absorbent assembly is not disposable) without having to dispose of, launder or otherwise replace the garment shell 22 with a new garment shell. More suitably, the front and back waist ends 138, 140 of the absorbent assembly 24 are releasably attached to the garment shell 22 generally at the front and back waist ends 56, 58 thereof, respectively. For example, fastening components 66 are attached to the outer cover 146 of the absorbent assembly 24 generally at the front waist end 138 thereof in laterally spaced relationship with each other. Corresponding laterally spaced complimentary fastening components 68 are attached to the inner surface of the garment shell 22 at the front waist end 56 thereof for releasable attachment to the fastening components 66 at the front waist end 138 of the absorbent assembly 24. Additional fastening components 66 can be attached to the outer cover 146 of the absorbent assembly 24 generally at the back waist end 140 thereof with corresponding fastening components 68 being attached to the inner surface of the back waist end 58 of the garment shell 22 for releasable attachment to the fastening components 66 at the back waist end of the absorbent assembly.

The fastening components 66, 68 can comprise any refastenable fasteners suitable for garments as described previously herein, such as adhesive fasteners, cohesive fasteners, mechanical fasteners, or the like. In particularly suitable embodiments the fastening components 66, 68 comprise mechanical fastening elements provided by interlocking geometric shaped materials such as hooks, loops, bulbs, mushrooms, arrowheads, balls on stems, male and female mating components, buckles, snaps, or the like. For example, in the illustrated embodiment the fastening components 66 attached to the front and back waist ends 138, 140 of the absorbent assembly 24 comprise hook fasteners and the fastening components 68 attached to the front and back waist ends 56, 58 of the garment shell 22 comprise complementary loop fasteners.

Alternatively, the fastening components 66 may comprise loop fasteners and the fastening components 68 may comprise complementary hook fasteners. In another embodiment, the fastening components 66, 68 can comprise interlocking similar surface fasteners, or adhesive and cohesive fastening elements such as an adhesive fastener and an adhesive-receptive landing zone or material, or the like. One skilled in the art will recognize that the shape, density and polymer composition of the hooks and loops may be selected to obtain the desired level of engagement between the fastening components 66, 68. A more aggressive hook material may comprise a material with a greater average hook height and/or a greater percentage of directionally-aligned hooks.

The fastening components 66, 68 are illustrated as being rectangular in shape, although it is understood that the fastening components may be square, circular, curved or other suitable shape. The fastening components 66, 68 suitably each have a width (e.g., determined parallel to the longitudinal axis of the garment 10 in the illustrated embodiment) in the range of about 3 mm to about 50 mm, and a length (e.g., determined parallel to the transverse axis of the garment 10 in the illustrated embodiment) in the range of about 20 mm to about 175 mm. However, it is contemplated that the fastening components 66, 68 may be larger or smaller in width and/or length without departing from the scope of this invention. It is also contemplated that single fastening components 66 may be attached to the absorbent assembly 24 at the respective front and back waist ends 138, 140. In such an embodiment, the single fastening components 66 may suitably be laterally positioned centrally on the absorbent assembly 24 at the respective waist ends 138, 140 thereof and may extend partially or fully across the full width of the absorbent assembly at the waist ends.

The fastening components 66 of the illustrated embodiment may be attached to the front and back waist ends 138, 140 of the absorbent assembly 24 by adhesive, by thermal bonding or ultrasonic bonding, or by any other suitable attachment technique. The fastening components 68 may be attached to the front and back waist ends 56, 58 of the garment shell 22 by any of these attachment techniques as well, and may be attached using the same attachment technique used to attach the fastening components 66 to the front and back waist ends 138, 140 of the absorbent assembly 24, or by a different attachment technique. It is also contemplated that the fastening components 66 may be attached to the front and back waist ends 138, 140 of the absorbent assembly 24 by being formed integrally therewith. Likewise, the fastening components 68 may be formed integrally with the respective front and back waist ends 56, 58 of the garment shell 22.

With the absorbent assembly 24 releasably attached to the garment shell 22, the elasticized side edges 136 of the absorbent assembly generally define laterally opposite elastic leg openings 170 of the absorbent assembly (broadly, inner leg openings of the absorbent garment 10) whereat the absorbent assembly provides an elastic fit against at least part of the wearer's legs. The waist ends 138, 140 of the absorbent assembly 24 together with the waist ends 56, 58 of the garment shell 22 together broadly define the waist opening 20 of the absorbent garment 10. The leg openings 40 of the garment shell 22 broadly define outer leg openings of the absorbent garment 10, separate (e.g., discrete) from the absorbent assembly leg openings 170, whereat the absorbent garment hangs generally loose about the wearer's legs.

While not shown in the drawings, it is contemplated that the absorbent assembly 24 may additionally be releasably attached to the garment shell 22 other than at the waist ends 138, 140 of the absorbent assembly and remain within the scope of this invention. For example, the absorbent assembly 24 may be secured to the garment shell longitudinally intermediate the waist ends 138, 140 of the absorbent assembly, e.g., and more suitably within the crotch region 126 of the absorbent assembly.

Figure 5:
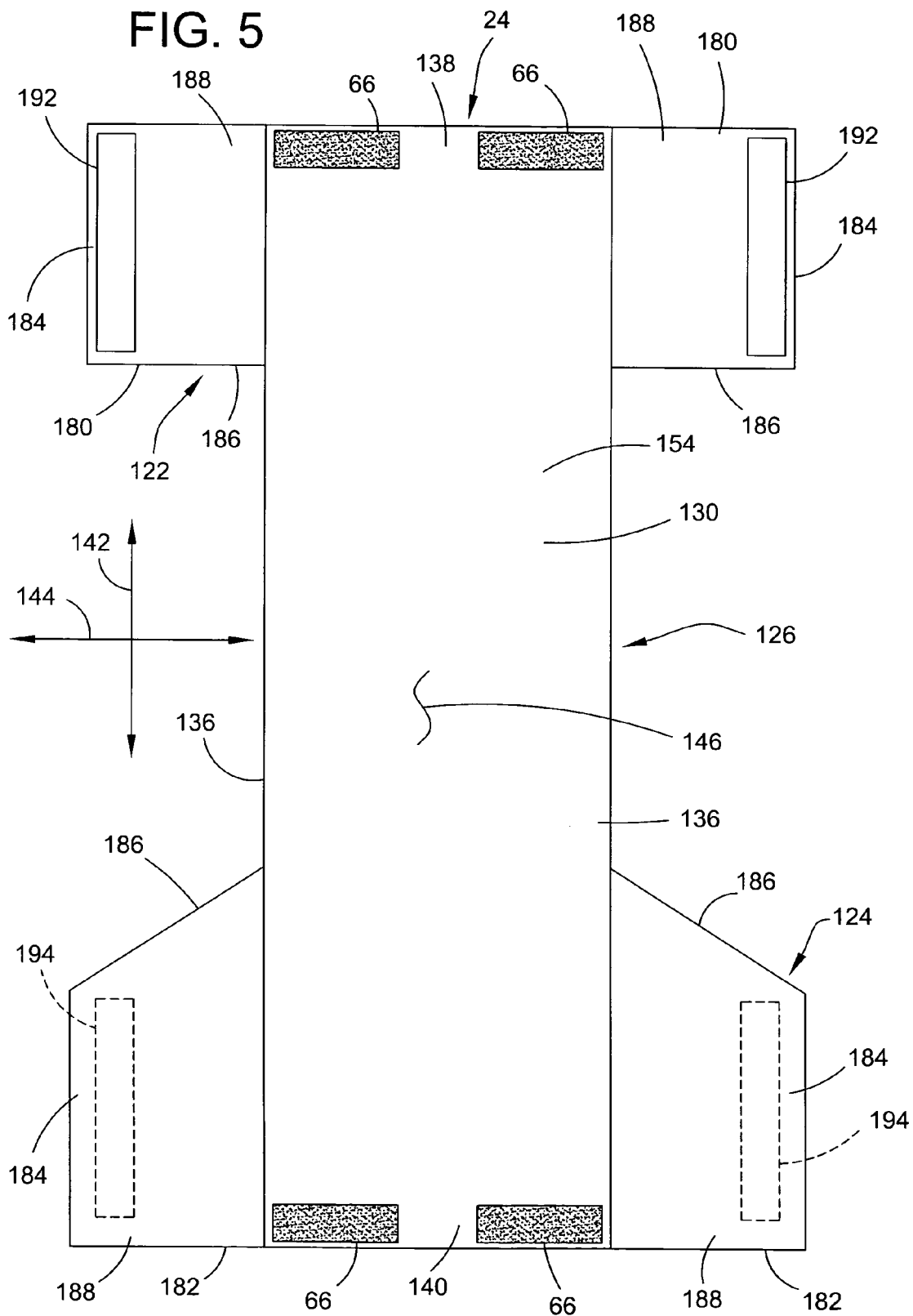
FIG. 5 is a plan view similar to FIG. 4a illustrating an alternative embodiment of an absorbent assembly.

In an alternative embodiment of the absorbent assembly 24 as shown in FIG. 5 (as well as in a second embodiment of an absorbent garment 10 shown in FIG. 6 and described further below), the absorbent assembly 24 may be a brief-style absorbent assembly such as children's training pants, swim pants or adult incontinence products which are configured for wearing about the full waist of the wearer. That is, the absorbent assembly 24 could be worn on the wearer's waist without being attached to the garment shell 22. More particularly, in addition to the components illustrated in FIG. 4 and described previously herein, the absorbent assembly 24 illustrated in FIGS. 5 and 6 further comprises front and back side panels, designated 180 and 182, respectively, disposed generally on each side of the absorbent assembly 24 at the respective front and back waist regions 122, 124 of the absorbent assembly and extending transversely outward therefrom. The side panels 180, 182 may be attached to the bodyside liner 148 and/or to the outer cover 146 of the absorbent assembly 24 by adhesive, or by thermal or ultrasonic bonding, or by other suitable attachment techniques known to those skilled in the art. Alternatively, the side panels 180, 182 can be formed as an integral portion of a component of the absorbent assembly 24. For example, the side panels 180, 182 can comprise a generally wider portion of the outer cover 146, the bodyside liner 148, and/or another component of the absorbent assembly 24.

The front and back side panels 180, 182 have respective outer edges 184 which broadly define the side edges of the absorbent assembly 24 at the front and back waist regions 122, 124 thereof. The side panels 180, 182 also have respective leg end edges 186 disposed toward the longitudinal center of the absorbent assembly 24, and respective waist end edges 188 which further define the respective front or back waist end 138, 140 of the absorbent assembly 24. The leg end edges 186 of the back side panels 182 are illustrated as being curved and/or angled relative to the transverse axis 144 to provide a better fit of the absorbent assembly 24 about the wearer's legs. However, it is understood that the leg end edges 186 of the front side panels 180 may additionally, or alternatively, be curved or angled, or none of the leg end edges may be curved or angled, without departing from the scope of this invention.

The side panels 180, 182 suitably comprise a stretchable material, and more suitably an elastic material, capable of stretching in a direction generally parallel to the transverse axis 144 of the absorbent assembly 24. Suitable elastic materials, as well as one process of incorporating elastic side panels into brief-style absorbent assemblies, are described in the following U.S. Patents: U.S. Pat. No. 4,940,464 issued Jul. 10, 1990 to Van Gompel et al.; U.S. Pat. No. 5,224,405 issued Jul. 6, 1993 to Pohjola; 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material may comprise a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference. Alternatively, the side panel material may comprise other woven or non-woven materials, such as those described above as being suitable for the outer cover 146 or bodyside liner 148; mechanically pre-strained composites; stretchable but inelastic (e.g., extensible) materials; or non-stretchable materials.

Figure 6:
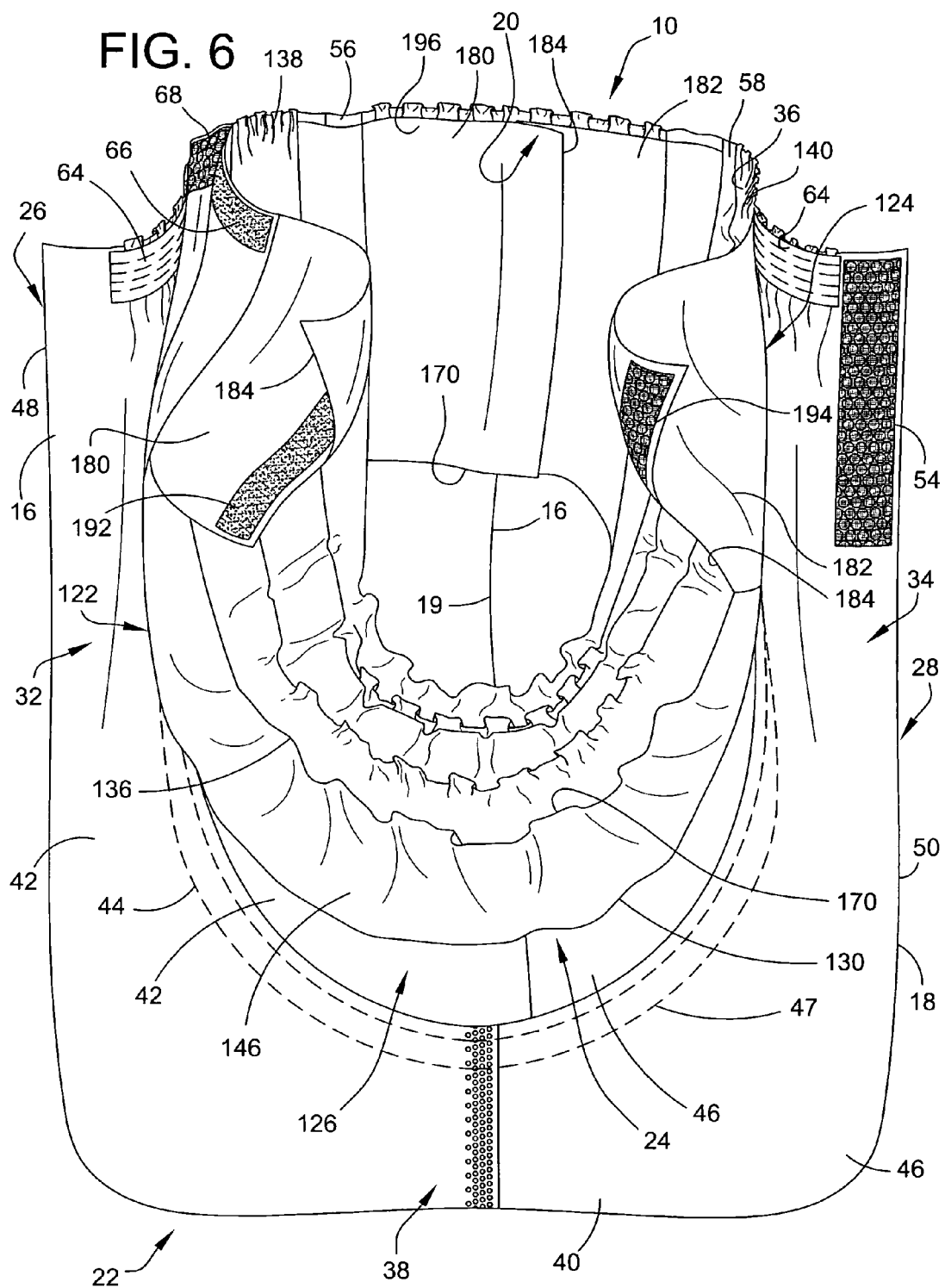
FIG. 6 is a side elevation of a second embodiment of an absorbent garment incorporating the absorbent assembly of FIG. 5, with a side seam of the absorbent garment shown in an unfastened condition and one pair of side panels of the absorbent assembly also shown in an unfastened condition.

Still referring to FIGS. 5 and 6, the absorbent assembly 24 of this embodiment further comprises laterally spaced first fastening components 192 attached to the front side panels 180 generally at the outer edges 184 thereof and complementary second fastening components 194 attached to the back side panels 182 generally at the outer edges thereof and adapted for refastenable engagement with the first fastening components to releasably attach the side panels together to thereby define a three-dimensional configuration of the absorbent assembly that can be worn about the waist of the wearer. The fastening components 192, 194 can comprise any of the refastenable fasteners previously described herein as being suitable for absorbent garments, such as adhesive fasteners, cohesive fasteners, mechanical fasteners, or the like. In particular embodiments the fastening components 192, 194 comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated embodiment, the first fastening components 192 comprise hook fasteners and the second fastening components 194 comprise complementary loop fasteners. Alternatively, the first fastening components 192 may comprise loop fasteners and the second fastening components 194 may comprise complementary hook fasteners. In another embodiment, the fastening components 192, 194 can comprise interlocking similar surface fasteners, or adhesive and cohesive fastening elements such as an adhesive fastener and an adhesive-receptive landing zone or material; or the like. It is also contemplated that the side panels 180, 182 of the absorbent assembly may instead be non-refastenably (e.g., permanently or frangibly) attached together, such as by adhesive, by thermal bonding or ultrasonic bonding, or by other suitable attachment techniques and remain within the scope of this invention.

In the illustrated embodiment, the back side panels 182 overlap the front side panels 180 upon releasable attachment of the side panels. However, it is understood that the front side panels 180 may instead overlap the back side panels 182 without departing from the scope of this invention. The side panels 180, 182 are otherwise unattached to the garment shell 22 so that upon assembling the absorbent garment 10, the side panels are attached to each other and then the side margins 48, 50 of the front and back panel assemblies 26, 28 of the garment shell 22 are separately attached to each other.

As shown in FIG. 6, with the side panels 180, 182 attached to each other to define the three-dimensional configuration of the absorbent assembly 24, the front and back waist ends 138, 140 of the absorbent assembly together define a waist opening 196 of the absorbent assembly separate from the waist opening 36 of the garment shell 22. In such an embodiment, the waist opening 196 of the absorbent assembly 24 broadly defines the waist opening 20 of the absorbent garment 10. The side edges 136 of the absorbent assembly 24, including the leg end edges 186 of the side panels 180, 182, define the elastic leg openings 170 (broadly, the inner leg openings of the absorbent garment 10) of the absorbent assembly 24 about which the absorbent assembly provides an elastic fit against the wearer's leg. The attached side margins 48, 50 of the front and back panel assemblies 26, 28 of the garment shell 22 broadly define the side margins 16, 18 of the absorbent garment 10 which are releasably attached along all or part of the side seams 19 of the absorbent garment. As in the embodiment of FIG. 3, the leg openings 40 of the garment shell 22 shown in FIG. 6 broadly define outer leg openings of the absorbent garment 10 separate (e.g., discrete) from the leg openings 170 of the absorbent assembly whereat the absorbent garment hangs generally loose about the wearer's legs.

Figure 7:
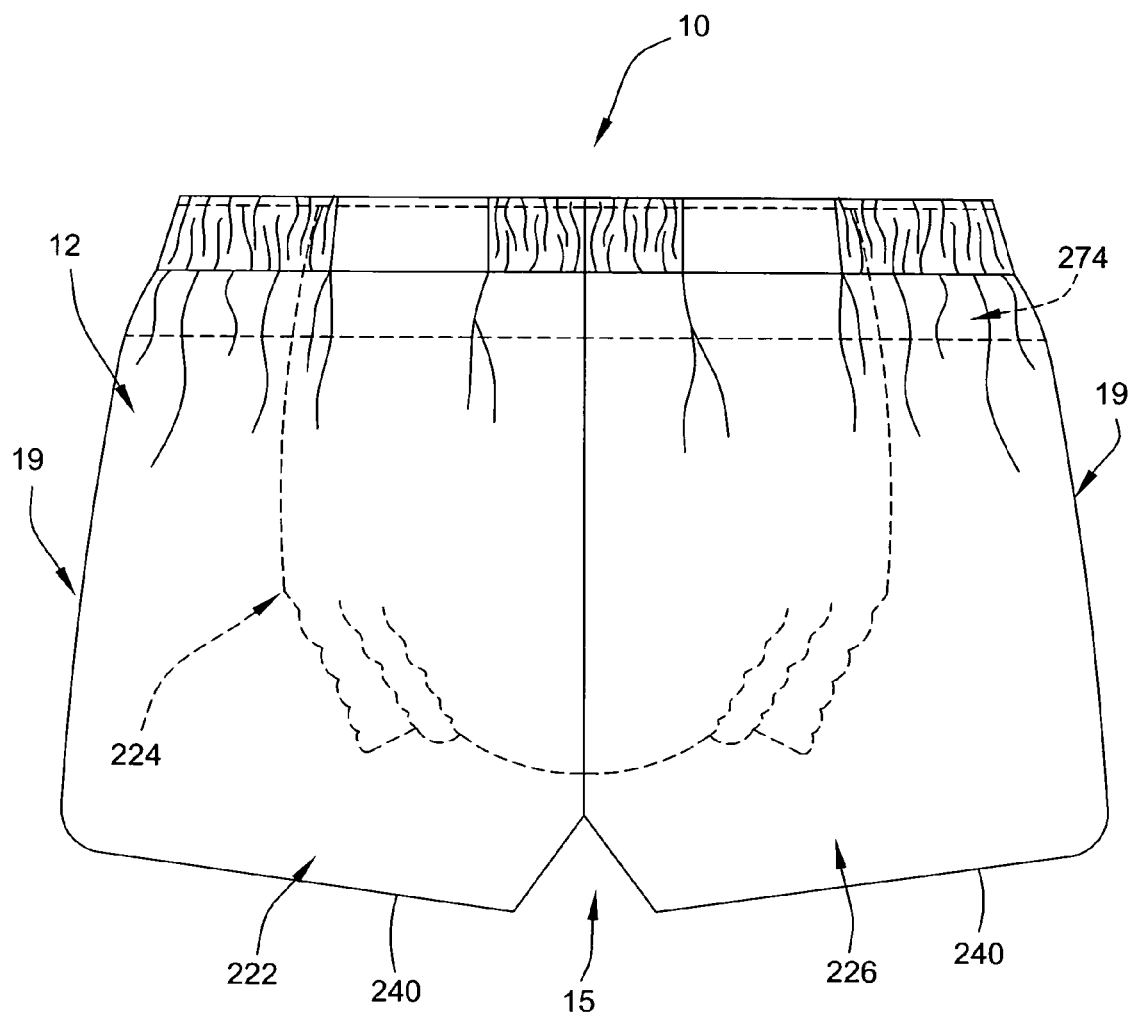
FIG. 7 is a front elevation of a third embodiment of an absorbent garment of the present invention.
Figure 8:
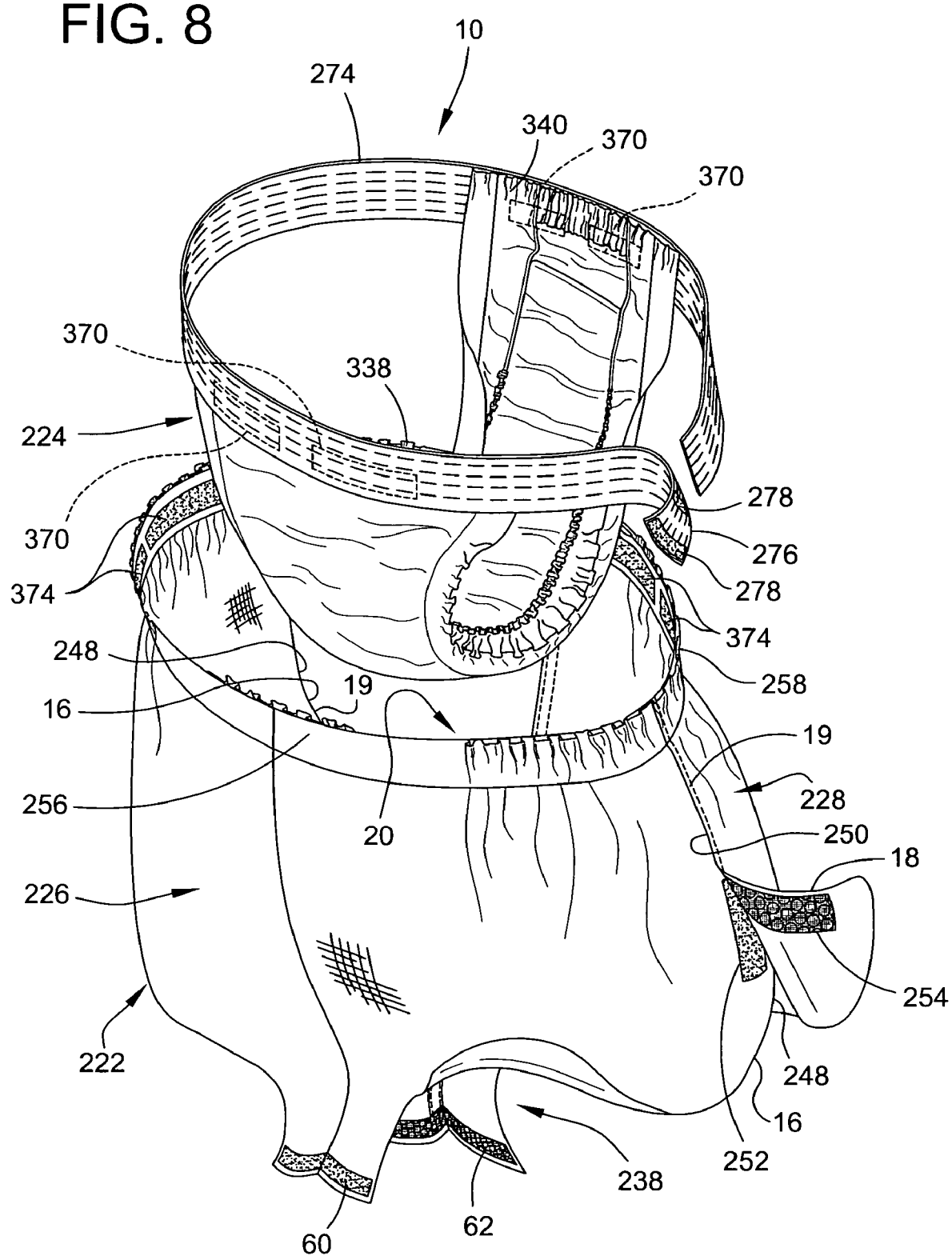
FIG. 8 is an exploded perspective of the absorbent garment of FIG. 7.

Referring now to FIGS. 7 and 8, an absorbent garment 10 according to another embodiment of the present invention comprises a garment shell, generally indicated at 222, an absorbent assembly, generally indicated at 224 disposed within the garment shell, and a waist belt, generally indicated at 274 and configured for extending about the waist of the wearer to provide a suitable fit of the absorbent garment on the wearer's waist. The waist belt 274 is suitably stretchable, and more suitably elastic. For example, the waist belt 274 is suitably stretchable to a length in the range of about 120 percent to about 200 percent of its unstretched length.

The waist belt 274 is suitably constructed of elastomeric materials including, but not limited to elastic strands, elastic films, nonwoven elastic webs, meltblown or spunbond elastomeric fibrous webs. Examples of suitable elastomeric materials include ESTANE® elastomeric polyurethanes (available from B.F. Goodrich and Company located in Cleveland, Ohio), PEBAX® elastomers (available from AtoChem located in Philadelphia, Pa.), HYTREL® elastomeric polyester (available from E.I. DuPont de Nemours located in Wilmington Del.), KRATON® elastomer (available from Kraton, Inc. of Houston, Tex.), strands of LYCRA® elastomer (available from E.I. DuPont de Nemours located in Wilmington Del.) or the like, as well as combinations thereof. Suitable elastomeric materials may be braided, knit, woven or otherwise combined with natural fibers, or synthetic fibers such as polyester, nylon or polyolefins.

Alternatively, the waist belt 274 may be constructed of an extensible material, or it may be constructed of a non-stretchable material, without departing from the scope of this invention. The waist belt 274 suitably has a width of at least about 6 mm, and more suitably in the range of about 20 mm to about 80 mm. As an example, the waist belt 274 shown in FIGS. 7 and 8 has a width of approximately 38 mm.

In the illustrated embodiment, the waist belt 274 is suitably sized in length so as to define an overlapping end portion 276 upon extending about the wearer's waist whereby the end portion overlaps an underlying portion (e.g., the portion extending about the wearer's waist) of the belt. Fastening components 278 can be attached to the overlapping end portion 276 of the waist belt 274 for use in releasably attaching the overlapping end portion of the belt to the underlying portion to secure the belt on the wearer's waist. For example, the waist belt 274 shown in FIG. 8 has a pair of fastening components 278, such as hook fasteners, spaced lengthwise from each other generally at the overlapping end portion 276 of the belt. The hook fasteners may be attached to the waist belt 274 by adhesive, or by thermal or ultrasonic bonding, or by other suitable attachment techniques.

The waist belt 274 material can also comprise a suitable loop material for releasable attachment of the hook fasteners thereto. It is understood that more than two fastening components 278 may be attached to the overlapping end portion 276 of the waist belt 274, or that a single fastening component may be secured to the waist belt and may extend longitudinally along all or part of the overlapping end portion of the waist belt. It is also understood that instead of the waist belt 274 material providing a suitable loop material, one or more complementary fastening components (not shown) may be attached to the underlying portion of the waist belt and adapted for releasable attachment to the fastening components 278 on the overlapping end portion 276 of the waist belt. In such an embodiment, the fastening components attached to the waist belt 274 may comprise any of the fastening components described previously herein as being suitable for absorbent garments. It is further contemplated that the overlapping end portion 276 of the waist belt 274 may be permanently attached to the underlying portion of the belt without departing from the scope of this invention.

The garment shell 222 is substantially similar to the garment shell 22 of FIGS. 1-3 in that it comprises front and back panel assemblies, generally indicated at 226 and 228, respectively, attached to each other at respective side margins 248, 250 to form the three-dimensional configuration of the garment shell. In the embodiment illustrated in FIGS. 7 and 8, the side margins 248, 250 of the front and back panel assemblies 226, 228 are permanently attached to each other generally from front and back waist ends 256, 258 of the garment shell 222 down to a position intermediate the waist ends and leg openings 240 of the garment shell (e.g., about half way between the waist ends and the leg openings in the illustrated embodiment). The side margins 248, 250 of the front and back panel assemblies 226, 228 are otherwise suitably releasably attached to each other, e.g., from the bottom of the permanent attachment down to the leg openings 240 of the garment shell 222, by suitable fastening components 252, 254 which are similar in construction to the fastening components 52, 54 of FIG. 2. Thus, it is understood that the side seams 19 of the absorbent garment 10 of this embodiment are releasably attached along only a lower portion of the side seams.

Alternatively, the front and back panel assemblies 226, 228 of the garment shell 222 may be attached in substantially the same manner as those shown in FIG. 2 and described previously herein. It is understood that the front and back panel assemblies 226, 228 may instead be permanently attached to each other along the full length of the side margins 248, 250, or they may be releasably attached to each other along the full length of the side margins. It is also contemplated that the front and back panel assemblies 226, 228 of the garment shell 222 may be permanently or releasably attached to each other along only a portion of the length of the side margins 248, 250 and be otherwise free from attachment along the remaining portion or portions of the side margins without departing from the scope of this invention. In the illustrated embodiment, the front and back panel assemblies 226, 228 are further releasably attached to each other at a crotch region 238 of the garment shell 222 by suitable fastening components 60, 62. However, it is understood that the front and back panel assemblies 226, 228 of the garment shell 222 may be permanently attached to each other at the crotch region 238, or that the crotch region of the garment shell may be omitted altogether (such as where the garment shell is intended to resemble a skirt).

The absorbent assembly 224 of the embodiment illustrated in FIGS. 7 and 8 is substantially the same as the absorbent assembly 24 of the embodiment of FIGS. 1-4a. Alternatively, the absorbent assembly 224 can be constructed substantially the same as the absorbent assembly 24 of the embodiment of FIGS. 5 and 6.

As seen best in FIG. 8, the absorbent assembly 224 can be releasably attached to an inner surface of the waist belt 274 by fastening components 370 attached to the outer surface of front and back waist ends 338, 340 of the absorbent assembly so that absorbent assembly is generally disposed between the waist belt and the wearer of the absorbent garment 10 during wear. As an example, in the illustrated embodiment the fastening components 370 attached to the front and back waist ends 338, 340 of the absorbent assembly 224 are hook fasteners. The waist belt 274 material provides a suitable loop material for releasable attachment to the hook fasteners 370 of the absorbent assembly 224. While two laterally spaced fastening components 370 (e.g., hook fasteners) are illustrated in FIG. 8 as being attached to each of the front and back waist ends 338, 340 of the absorbent assembly 224, it is understood that a single fastening component may be attached to each of the front and back waist ends of the absorbent assembly and extend laterally across all or part of the respective waist end without departing from the scope of this invention.

In an alternative embodiment (not shown), the waist belt 274 may comprise one or more complementary fastening components (not shown) attached to the waist belt inner surface for releasable attachment to the fastening components 370 attached to the front and back waist ends 338, 340 of the absorbent assembly 224. In such an embodiment, the fastening components attached to the waist belt 274 and to the absorbent assembly 224 may comprise any of the fastening components previously described herein as being suitable for absorbent garments. It is also contemplated that the absorbent assembly 224 may instead be releasably attached to the outer surface of the waist belt 274 without departing from the scope of this invention.

The garment shell 222 is suitably releasably attached to the outer surface of the waist belt 274, such as by fastening components 374 attached to the inner surface of the garment shell generally at the front and back waist ends 256, 258 thereof. For example, the fastening components 374 of the illustrated embodiment comprise hook fasteners and the waist belt 274 material provides a suitable loop material for releasable attachment to the hook fasteners. However, it is understood that the waist belt 274 may have one or more fastening components (not shown) attached to its outer surface for releasable attachment to the fastening components 374 attached to the front and back waist ends 256, 258 of the garment shell 222. In such an embodiment, the fastening components attached to the garment shell 222 and to the outer surface of the waist belt 274 may comprise any of the fastening components described previously herein as being suitable for absorbent garments. Alternatively, the garment shell 222 may be permanently attached to the waist belt 274 (except for the overlapping end portion of the waist belt), such as by adhesive, by thermal or ultrasonic bonding, or by other suitable attachment technique, without departing from the scope of this invention.

The absorbent garment 10 of FIGS. 7 and 8 can be placed on the wearer in generally any order. In one suitable embodiment, the waist belt 274 can be extended about the wearer's waist and the overlapping end portion 276 fastened to the underlying portion to secure the waist belt on wearer's waist. The absorbent assembly 224 can then be releasably attached to the waist belt 274, followed by the garment shell 222 being attached to the waist belt over the absorbent assembly. Where the garment shell 222 is permanently attached to the waist belt 274 instead of releasably attached, the garment shell is permanently attached to the waist belt before the waist belt is extended around the wearer's waist and fastened in place. In such an embodiment, the absorbent assembly 224 can be attached to the waist belt 274 and the entire garment 10 can be placed on the wearer as a fully assembled unit. Alternatively, the absorbent assembly 224 can be put in place on the wearer and attached to the waist belt 274 1) wherein the waist belt and garment shell 222 are already in place on the wearer or 2) wherein the waist belt is subsequently extended about the wearer such that the absorbent assembly becomes attached to the waist belt as the belt is placed around the wearer's waist.

Figure 9:
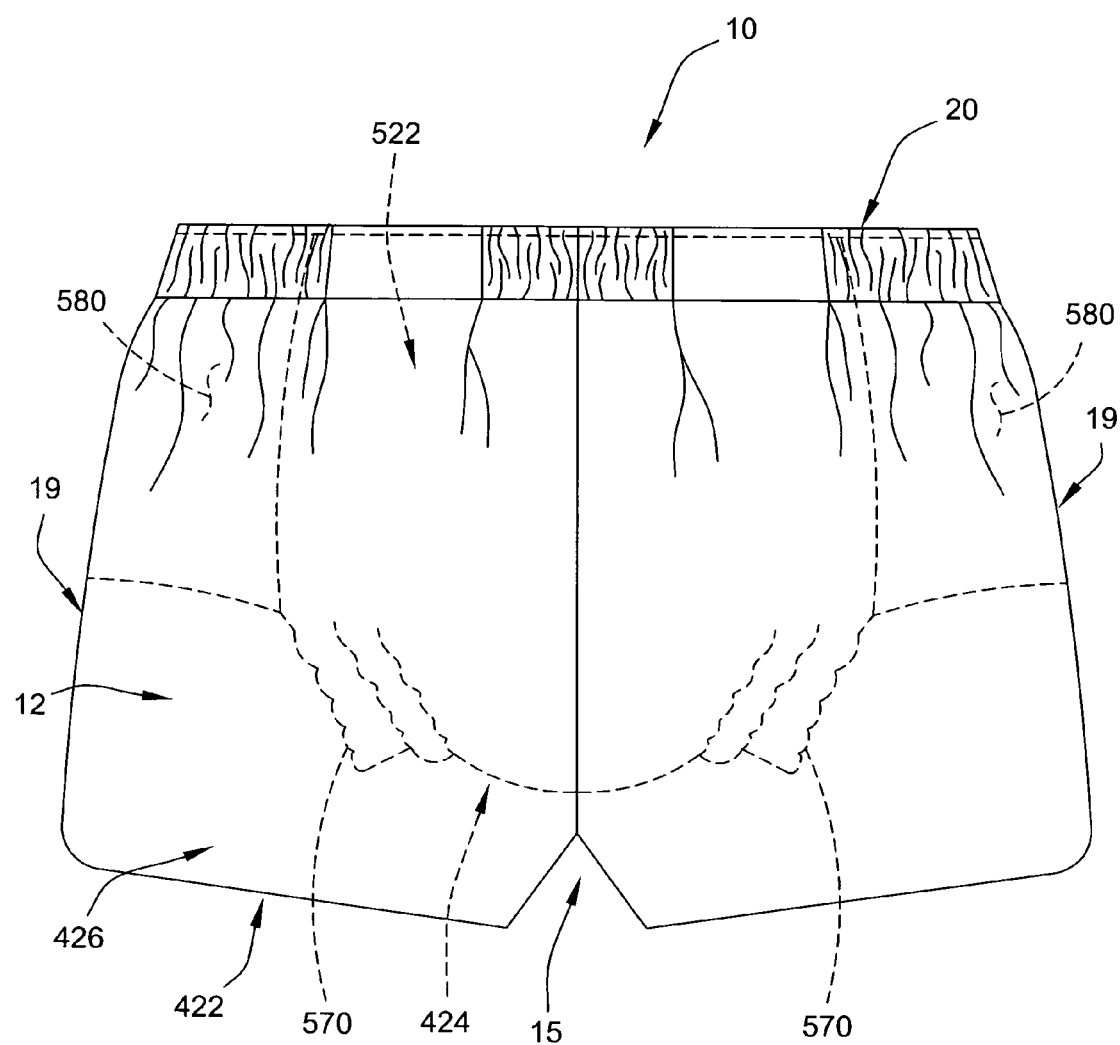
FIG. 9 is a front elevation of a fourth embodiment of an absorbent garment of the present invention.
Figure 10:
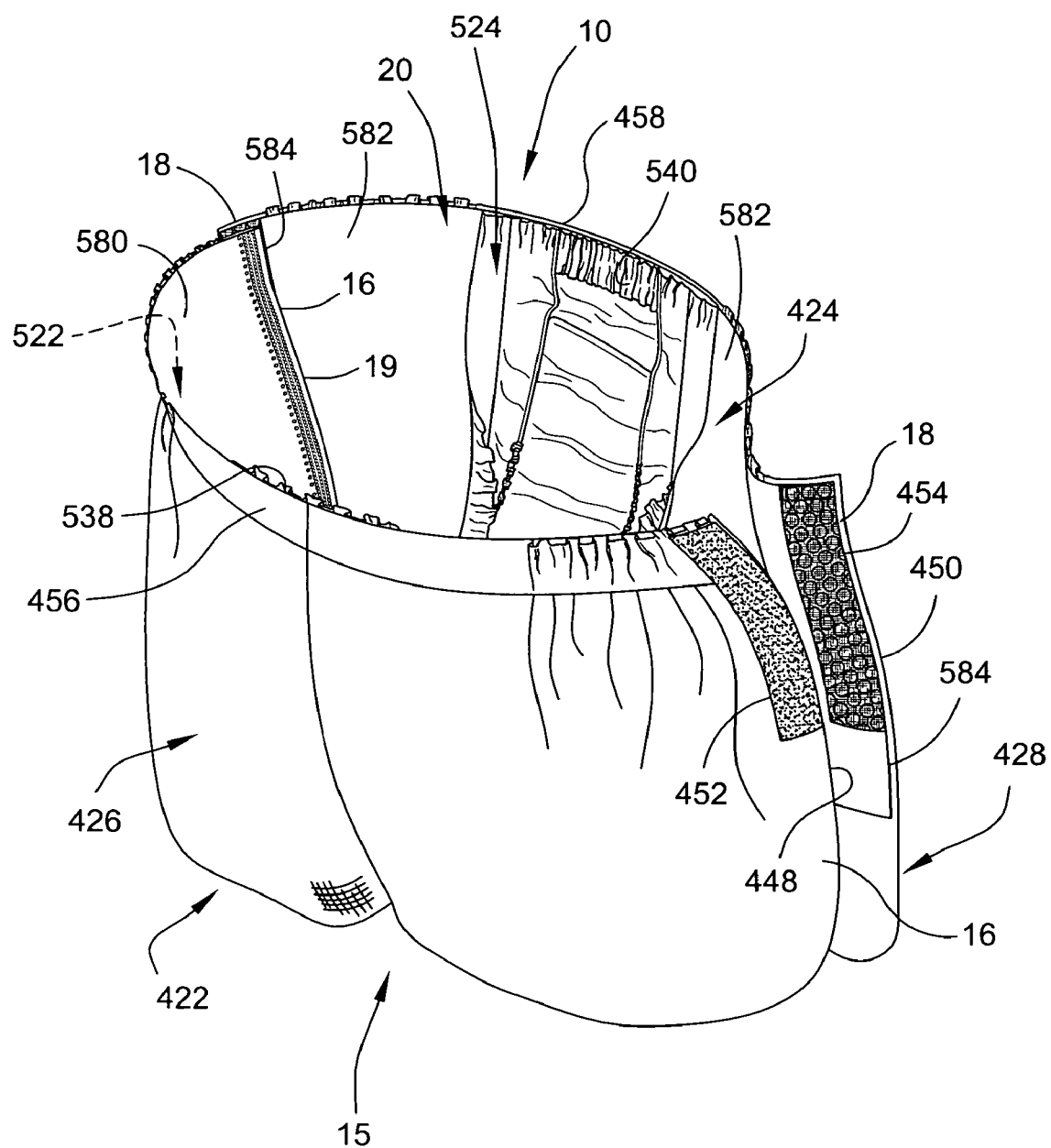
FIG. 10 is a perspective of a fifth embodiment of an absorbent garment of the present invention, with a side seam of the absorbent garment shown in an unfastened condition.

FIGS. 9 and 10 illustrate another embodiment of an absorbent garment 10 comprising a garment shell, generally indicated at 422, and an absorbent assembly, generally indicated at 424 disposed within the garment shell. The absorbent assembly 424 is substantially the same as the absorbent assembly 24 shown in FIGS. 5-6 and described previously herein as a brief-style absorbent assembly having refastenable front and back side panels 580, 582, respectively. The garment shell 422 comprises front and back panel assemblies, generally indicated at 426 and 428, respectively, constructed in a manner substantially similar to the front and back panel assemblies 26, 28 of the garment shell 22 of FIGS. 2 and 3 but with the waist elastic members 64 of FIG. 2 omitted from the garment shell of FIGS. 9 and 10.

In this embodiment, the absorbent assembly 424 is at least in part permanently attached to the garment shell 422 so that the entire absorbent garment 10 is disposable (or must be otherwise laundered if the absorbent assembly is re-usable). More particularly, front side panels 580 of the absorbent assembly 424 are permanently attached generally at outer edges 584 (FIG. 10) thereof (broadly, the outer edges of the absorbent assembly at a front waist region 522 thereof) to respective side margins 448 of front panel assembly 426 of the garment shell 422. For example, the front side panels 580 of the absorbent assembly 424 may be attached to the front panel assembly 426 of the garment shell 422 by adhesive, or by thermal or ultrasonic bonding, or by other suitable attachment techniques. Back side panels 582 are permanently attached generally at outer edges 584 (FIG. 10) thereof (broadly, outer edges of the absorbent assembly at a back waist region 524 (FIG. 10) thereof) to respective side margins 450 of the back panel assembly of the garment shell 422 in a like manner. In this embodiment, the permanently attached front side panels 580 of the absorbent assembly 424 and front panel assembly 426 of the garment shell 422 together broadly define the front side margins 16 of the absorbent garment 10 and the permanently attached back side panels 582 and back panel assembly 428 together broadly define the back side margins 450 of the absorbent garment.

Laterally opposite first fastening components 452 are attached to the front side margins 16 of the absorbent garment 10 (i.e., where the front side panels 580 are attached to the side margins 448 of the front panel assembly 426 of the garment shell 422). The first fastening components 452 are adapted for refastenable engagement with corresponding laterally opposite second fastening components 454 which are attached to the back side margins 18 of the absorbent garment 10 (e.g., where the back side panels 582 are attached to the side margins 450 of the back panel assembly 428 of the garment shell 422) to releasably attach the front and back side margins of the absorbent garment.

The fastening components 452, 454 can comprise any refastenable fasteners described previously herein as being suitable for absorbent garments, such as adhesive fasteners, cohesive fasteners, mechanical fasteners, or the like. In particular embodiments the fastening components 452, 454 comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated embodiment, the first fastening components 452 comprise hook fasteners and the second fastening components 454 comprise complementary loop fasteners. Alternatively, the first fastening components 452 may comprise loop fasteners and the second fastening components 454 may comprise complementary hook fasteners. In another embodiment, the fastening components 452, 454 can comprise interlocking similar surface fasteners, or adhesive and cohesive fastening elements such as an adhesive fastener and an adhesive-receptive landing zone or material; or the like.

More particularly, in the illustrated embodiment the first fastening components 452 are attached to the outer surface of the front panel assembly 426 of the garment shell 422 generally at the side margins 448 thereof, such as by adhesive, or by thermal or ultrasonic bonding, or by another suitable attachment technique. The second fastening components 454 are attached in a similar manner to inner surfaces of the back side panels 582 of the absorbent assembly 424 generally at the outer edges 584 of the side panels. In this manner, the back side margins 18 of the absorbent garment 10 overlap the front side margins 16 of the absorbent garment upon releasable attachment of the fastening components 452, 454. However, the absorbent garment 10 can alternatively be configured so that the front side margins 16 of the absorbent garment overlap the back side margins 18 thereof upon releasably attaching the fastening components 452, 454 without departing from the scope of this invention. For example, the first fastening components 452 may be attached to the outer surface of the garment shell 422 at the side margins 448 thereof and the second fastening components 454 may be attached to the back side panels 582 of the absorbent assembly 424.

The amount of overlap between the front and back side margins 16, 18 of the absorbent garment 10 is suitably in the range of about 0.1 inches to about 6 inches (about 2.5 mm to about 152.4 mm), and more suitably in the range of about 0.5 inches to about 3 inches (about 12.7 mm to about 76.2 mm). It is contemplated that the fastening components 452, 454 attached to at least one of the front and back side margins 16, 18 of the absorbent garment 10 may have a width corresponding to the range of overlap to permit a variable fit of the absorbent garment over a relatively wide range of wearer sizes. It is also contemplated that the first and second fastening components 452, 454 may be attached respectively to the front side panels 580 and the back side panels 582 of the absorbent assembly 424 generally at the outer edges 584 so that no overlapping of the front and back side margins 16, 18 of the absorbent garment 10 occurs upon releasable attachment of the fastening components.

The absorbent assembly 424 of the illustrated embodiment of FIGS. 9 and 10 is additionally permanently attached to the garment shell 422 generally at front and back waist ends 538, 540 of the absorbent assembly substantially across the entire width of the absorbent assembly at the front and back waist ends. The absorbent assembly 424 may be permanently attached to the garment shell 422 generally at the front and back waist ends 538, 540 of the absorbent assembly in the same manner as the side panels 580, 582, or by a different suitable attachment technique.

More suitably, the absorbent assembly 424 is permanently attached to the garment shell 422 generally at the front and back waist ends 538, 540 of the absorbent assembly by being operatively joined thereto. That is, the absorbent assembly 424 at the front and back waist ends 538, 540 can be stretched (including the side panels 580, 582 where the side panels are constructed of an elastic material) and then attached to respective front and back waist ends 456, 458 of the garment shell 422, such as by adhesive, by thermal or ultrasonic bonding, or by other suitable attachment techniques. Upon retraction of the absorbent assembly 424 following attachment, the front and back waist ends 456, 458 of the garment shell 422 become elastically gathered to provide a gathered appearance of the garment shell about the wearer's waist.

It is also understood that the front and back waist ends 538, 540 of the absorbent assembly 424 may be permanently attached to the garment shell 422 across only a portion of the front and/or back waist end of the absorbent assembly, or the absorbent assembly may be free from permanent attachment to the garment shell across the front and/or back waist end without departing from the scope of this invention. For example, where the front and back waist ends 538, 540 of the absorbent assembly 424 are free from attachment to the garment along all or part of the width of the absorbent assembly at the waist ends, one or more elastic members (not shown but similar to the elastic members 64 shown in FIGS. 2 and 3) may be attached to the garment shell 422 (e.g., on the inner surface thereof facing the absorbent assembly) along the extent of unattachment between the absorbent assembly and garment shell to provide elastic gathering of the garment shell without operatively joining the garment shell to the absorbent assembly.

Upon releasable attachment of the side margins 16, 18 of the absorbent garment 10 as shown in FIGS. 9 and 10, the side edges of the absorbent assembly 424 define elastic leg openings 570 (FIG. 9) (broadly, the inner leg openings of the absorbent garment 10) of the absorbent assembly about which the absorbent assembly provides an elastic fit against the wearer's leg. As in the embodiment of FIGS. 2 and 3, the leg openings of the garment shell 422 shown in FIGS. 9 and 10 broadly define outer leg openings of the absorbent garment 10 separate (e.g., discrete) from the leg openings 570 of the absorbent assembly 424 whereat the absorbent garment hangs generally loose about the wearer's legs.

Figure 11:
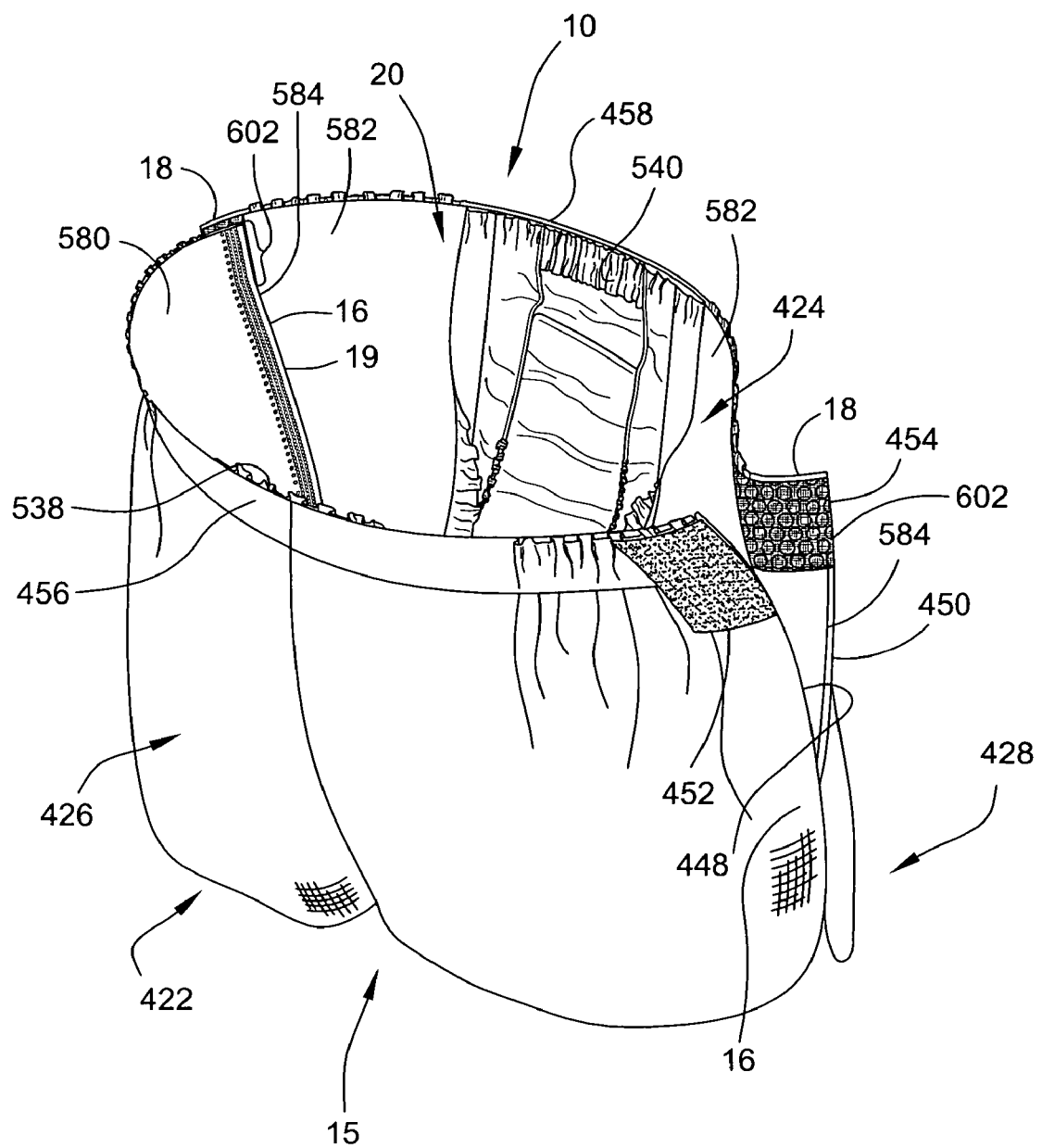
FIG. 11 is a perspective of a sixth embodiment of an absorbent garment of the present invention, with a side seam of the absorbent garment shown in an unfastened condition.

FIG. 11 illustrates another embodiment of an absorbent garment 10 that is substantially similar to the embodiment illustrated in FIGS. 9 and 10. However, in this embodiment the front and back side margins 16, 18 of the absorbent garment 10 are releasably attached to each other along only a small upper segment 602 thereof (e.g., a small upper portion of the side seams 19). For example, the upper segment 602 may suitably have a length at least equal to and more suitably greater than the width of the waist elastic 158 where the waist elastic is present. As another example, the side margins 16, 18 of the absorbent garment are suitably attached along a segment 602 extending generally from the front and back waist ends 456, 458 of the garment shell 422 a length of less than about 50 percent of the length of the side margins 448, 450 of the front and back panel assemblies 426, 428 of the garment shell. The side margins 16, 18 are otherwise substantially free from engagement along the remaining length of the side margins (e.g., between the releasable attachment and the leg openings of the absorbent garment 10). Upon releasable attachment of the side margins 16, 18 of the absorbent garment 10 in this embodiment, the absorbent garment is configured as a pair of running shorts.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. An absorbent garment for personal wear about the wearer's waist, said absorbent garment comprising:
    a garment shell configured for encircling the wearer's waist and having a front waist region, a front waist end at said front waist region, a back waist region and a back waist end at said back waist region; and
    an absorbent assembly disposed within the garment shell and constructed to take in and retain body exudates released by the wearer, the absorbent assembly having an inner surface adapted for contiguous relationship with the wearer's body, an outer surface, a front waist region in opposed relationship with the front waist region of the garment shell, a back waist region in opposed relationship with the back waist region of the garment shell, a crotch region extending longitudinally between and interconnecting the front waist region of the absorbent assembly and the back waist region of the absorbent assembly, a front waist end and a back waist end, the absorbent assembly being releasably and refastenably attached generally at its front waist end to the garment shell generally at the front waist end of the garment shell, said absorbent assembly also being releasably and refastenably attached generally at its back waist end to the garment shell generally at the back waist end of the garment shell such that the absorbent assembly is selectively detachable from and reattachable to the garment shell.

2. An absorbent garment as set forth in claim 1 wherein the absorbent garment has at least one outer leg opening and a pair of inner leg openings separate from and disposed within the garment shell, the absorbent assembly at least in part defining said inner leg openings of the absorbent garment, said garment shell defining said at least one outer leg opening of the absorbent garment.

3. An absorbent garment as set forth in claim 2 wherein the absorbent assembly is configured to provide an elastic fit of the absorbent assembly against the wearer's legs at the inner leg openings of the absorbent garment, the garment shell being configured to generally hang loose about the wearer's legs at the at least one outer leg opening of the absorbent garment.

4. An absorbent garment as set forth in claim 2 wherein the absorbent assembly is configured to encircle the legs of the wearer and fully defines the inner leg openings of the absorbent garment.

5. An absorbent garment as set forth in claim 2 wherein the garment shell further has a crotch region extending longitudinally between the front and back waist regions of the garment shell, the crotch region of the garment shell at least in part defining a pair of outer leg openings of the absorbent garment which are separate from the inner leg openings of the absorbent garment.

6. An absorbent garment as set forth in claim 5 wherein the crotch region of the absorbent assembly is free from attachment to the crotch region of the garment shell.

7. An absorbent garment as set forth in claim 1 further comprising at least one waist elastic member operatively joined to at least one of the front waist end of the absorbent assembly, the back waist end of the absorbent assembly, the front waist end of the garment shell and the back waist end of the garment shell to provide an elastic fit of the absorbent garment against the wearer's waist.

8. An absorbent garment as set forth in claim 1 wherein the absorbent garment has a waist opening, the front and back waist ends of the absorbent assembly at least in part defining the waist opening of the absorbent garment.

9. An absorbent garment as set forth in claim 1 wherein the absorbent assembly is configured to encircle the waist of the wearer generally at the front and back waist ends of the absorbent assembly to fully define the waist opening of the absorbent garment.

10. An absorbent garment as set forth in claim 9 wherein the absorbent assembly is a brief-style absorbent assembly.

11. An absorbent garment as set forth in claim 1 wherein the garment shell has a configuration selected from the group comprising shorts, skorts, skirts and swim trunks.

12. An absorbent garment as set forth in claim 1 wherein the absorbent garment has a waist opening, at least one outer leg opening, and laterally opposite side seams extending generally from the waist opening to said at least one outer leg opening, the absorbent garment being releasable and refastenable along at least a portion of each of said side seams.

13. An absorbent garment as set forth in claim 12 wherein the absorbent garment is permanently closed along another portion of each of said side seams.

14. An absorbent garment as set forth in claim 12 wherein the absorbent garment has a length from the waist opening to the at least one leg opening, the releasable and refastenable portion of each side seam comprising in the range of about 25 percent to about 50 percent of said length.

15. An absorbent garment as set forth in claim 12 wherein the garment shell comprises a front panel assembly having laterally opposite side margins and a back panel assembly having corresponding laterally opposite side margins, the front panel assembly being in generally overlapping relationship with the back panel assembly at the side margins of said front and back panel assemblies whereby the overlapped side margins generally define the side seams of the absorbent garment, the side margins being releasably and refastenably attached to each other along at least a portion of a length of said side margins to define the releasable and refastenable portion of the side seams of the absorbent garment.

16. An absorbent garment as set forth in claim 12 wherein the side seams of the absorbent garment are releasable and refastenable along the full length of the side seams from the waist opening of the absorbent garment to the at least one outer leg opening thereof.

17. An absorbent garment as set forth in claim 4 wherein the absorbent assembly has laterally opposite outer edges at the front waist region of the absorbent assembly and corresponding laterally opposite outer edges at the back waist region of the absorbent assembly, the front and back waist regions of the absorbent assembly being attached to each other generally at the respective outer edges of the front and back waist regions whereby the front and back waist regions of the absorbent assembly together with the crotch region of the absorbent assembly encircle the wearer's legs and define the inner leg openings of the absorbent garment.

18. An absorbent garment as set forth in claim 17 wherein the front and back waist regions of the absorbent assembly are releasably and refastenably attached at the respective outer edges of said front and back waist regions.

19. An absorbent garment as set forth in claim 4 wherein the absorbent assembly further comprises a pair of laterally opposite front side panels extending outward of the absorbent assembly generally at the front waist region on laterally opposite sides thereof, and a pair of laterally opposite back side panels extending outward of the absorbent assembly generally at the back waist region on laterally opposite sides thereof, each of the front side panels being attached to a corresponding one of the back side panels such that the front and back side panels together with the crotch region of the absorbent assembly together fully define the inner leg openings of the absorbent garment.

20. An absorbent assembly as set forth in claim 19 wherein each of the front side panels of the absorbent assembly is releasably and refastenably attached to a corresponding one of the back side panels of the absorbent assembly.

21. An absorbent garment as set forth in claim 20 wherein the garment shell comprises a front panel assembly having laterally opposite side margins and a back panel assembly having corresponding laterally opposite side margins, the front panel assembly being releasably and refastenably attached to the back panel assembly generally at the respective side margins thereof.

22. An absorbent garment as set forth in claim 1 wherein the absorbent garment has laterally opposite front side margins and corresponding laterally opposite back side margins, the front side margins and the back side margins being in overlapping relationship with each other to define laterally opposite side seams of the absorbent garment, the amount of overlap of the front side margins with the back side margins being in the range of about 0.1 inches (2.5 mm) to about 6 inches (152.4 mm)

23. An absorbent garment as set forth in claim 22 wherein the amount of overlap of the front side margins with the back side margins is in the range of about 0.5 inches (12.7 mm) to about 3 inches (76.2 mm)

24. An absorbent garment as set forth in claim 1 wherein the absorbent assembly comprises a liquid permeable liner defining the inner surface of the absorbent assembly adapted for contiguous relationship with the wearer, an outer cover in generally opposed relationship with the liner and defining the outer surface of the absorbent assembly, and an absorbent body disposed between the liner and the outer cover.

25. An absorbent garment as set forth in claim 24 wherein the outer cover of the absorbent assembly is liquid impermeable and the garment shell is liquid permeable.

* * * * *